(12) United States Patent
Metz et al.

(10) Patent No.: US 10,128,448 B2
(45) Date of Patent: Nov. 13, 2018

(54) TRANSITION METAL COMPLEXES WITH CARBENE LIGANDS AND THE USE THEREOF IN OLEDS

(71) Applicant: UDC Ireland Limited, Dublin (IE)

(72) Inventors: Stefan Metz, Mannheim (DE); Thomas Geβner, Heidelberg (DE); Korinna Dormann, Bad Dürkheim (DE); Glauco Battagliarin, Mannheim (DE); Peter Murer, Oberwil (CH); Ute Heinemeyer, Neustadt (DE); Christian Lennartz, Schifferstadt (DE); Gerhard Wagenblast, Wachenheim (DE)

(73) Assignee: UDC Ireland Limited, Dublin (IE)

( * ) Notice: Subject to any disclaimer, the term of this patent is extended or adjusted under 35 U.S.C. 154(b) by 417 days.

(21) Appl. No.: 14/786,507

(22) PCT Filed: Apr. 28, 2014

(86) PCT No.: PCT/EP2014/058611
§ 371 (c)(1),
(2) Date: Oct. 22, 2015

(87) PCT Pub. No.: WO2014/177518
PCT Pub. Date: Nov. 6, 2014

(65) Prior Publication Data
US 2016/0072081 A1   Mar. 10, 2016

(30) Foreign Application Priority Data

Apr. 29, 2013 (EP) .................... 13165738

(51) Int. Cl.
| | | |
|---|---|---|
| *C09K 11/06* | (2006.01) | |
| *H01L 51/54* | (2006.01) | |
| *H01L 51/00* | (2006.01) | |
| *C07F 15/00* | (2006.01) | |
| *C09B 57/10* | (2006.01) | |
| *C09K 11/02* | (2006.01) | |
| *H01L 27/32* | (2006.01) | |
| *C09B 57/00* | (2006.01) | |
| *H01L 51/50* | (2006.01) | |

(52) U.S. Cl.
CPC ...... *H01L 51/0085* (2013.01); *C07F 15/0033* (2013.01); *C07F 15/0086* (2013.01); *C09B 57/00* (2013.01); *C09B 57/10* (2013.01); *C09K 11/025* (2013.01); *C09K 11/06* (2013.01); *H01L 27/3206* (2013.01); *H01L 51/0087* (2013.01); *C09K 2211/185* (2013.01); *H01L 51/5012* (2013.01); *H01L 51/5016* (2013.01); *H01L 51/5056* (2013.01); *H01L 51/5072* (2013.01); *H01L 51/5096* (2013.01); *Y02E 10/549* (2013.01)

(58) Field of Classification Search
CPC ... C09K 11/025; C09K 11/06; C09K 2211/00; C09K 2211/10; C09K 2211/1025; C09K 2211/1059; C09K 2211/18; C09K 2211/185; C09B 57/00; C09B 57/10; Y02E 10/549; C07F 15/00; C07F 15/0006; C07F 15/0033; C07F 15/0086; H01L 27/3206; H01L 51/0032; H01L 51/005; H01L 51/0051; H01L 51/0062; H01L 51/0084; H01L 51/0087; H01L 51/50; H01L 51/5012; H01L 51/5016; H01L 51/5056; H01L 51/5072; H01L 51/5096
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

2011/0187265 A1   8/2011   De Cola et al.

FOREIGN PATENT DOCUMENTS

| CN | 101652375 A | 2/2010 |
|---|---|---|
| CN | 102099365 A | 6/2011 |
| WO | 20110139704 | 11/2011 |

OTHER PUBLICATIONS

Brown, D.G. et al., "Stabilization of Ruthenium Sensitizers to TiO2 Surfaces through Cooperative Anchoring Groups", J. Am. Chem. Soc., 2013, vol. 135, pp. 1692-1695.

(Continued)

*Primary Examiner* — Andrew K Bohaty
(74) *Attorney, Agent, or Firm* — Riverside Law LLP

(57) ABSTRACT

The present invention relates to iridium and platinum carbene complexes of the general formula (I), to OLEDs (Organic Light-Emitting Diodes) which comprise such complexes, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker.

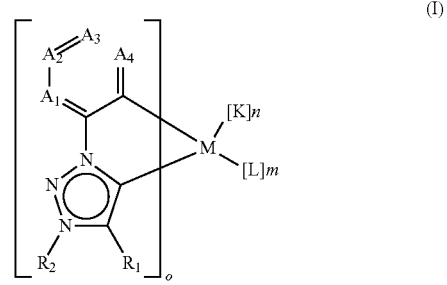

(I)

20 Claims, No Drawings

(56) References Cited

OTHER PUBLICATIONS

Donnelly, K.F. et al., "Regioselective Electrophilic C—H Bond Activation in Triazolylidene Metal Complexes Containing a N-Bound Phenyl Substituent", Organometallics, 2012, vol. 31, pp. 8414-8419.

Mathew, P. et al., "1,2,3-Triazolylidenes as Versatile Abnormal Carbene Ligands for Late Transition Metals", J. Am. Chem. Soc., 2008, vol. 130, No. 41, pp. 13534-13535.

TRANSITION METAL COMPLEXES WITH CARBENE LIGANDS AND THE USE THEREOF IN OLEDS

CROSS-REFERENCE TO RELATED APPLICATIONS

This application is a National Stage Entry of International Application PCT/EP2014/058611 filed Apr. 28, 2014, which claims priority to EP 13165738.9 filed Apr. 29, 2013, wherein the contents of all foregoing applications are herein incorporated by reference in their entirety.

FIELD OF THE INVENTION

The present invention relates to iridium and platinum complexes with monoanionic bidentate carbene ligands, to OLEDs (Organic Light-Emitting Diodes) which comprise such complexes, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker.

BACKGROUND OF THE INVENTION

Organic light-emitting diodes (OLEDs) exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cellphones, smartphones, digital cameras, mp3 players, laptops, etc. In addition, white OLEDs give great advantages over the illumination technologies known to date, especially a particularly high efficiency.

The prior art proposes numerous materials which emit light on excitation by electrical current.

P. Mathew et al., (J. Am. Chem. Soc., 2008, 130, 13534) reported the synthesis of 1,2,3-triazolylidenes, also known as abnormal carben or mesoionic carbine, and their use as versatile carbene ligands for late transition metals. Among others the synthesis of the following iridium carbene complex is described:

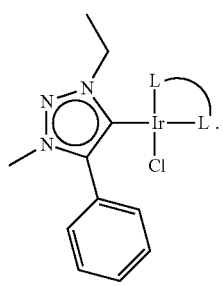

(L---L = COD)

The abnormal triazolylidene complexes are expected to have a great potential for the development of new catalysts.

WO2011/139704A2 discloses the use of transition metal complexes comprising 1,2,3-triazolylidene carbenes, focusing mainly on monodentate ligands for catalytic applications.

K. F. Donnelly et al. (Organometallics, 2012, 31, 8414) reported the use of bidentate ligands bearing one 1,2,3-triazolylidene carbene moiety coordinating to platinum and iridium metal centers:

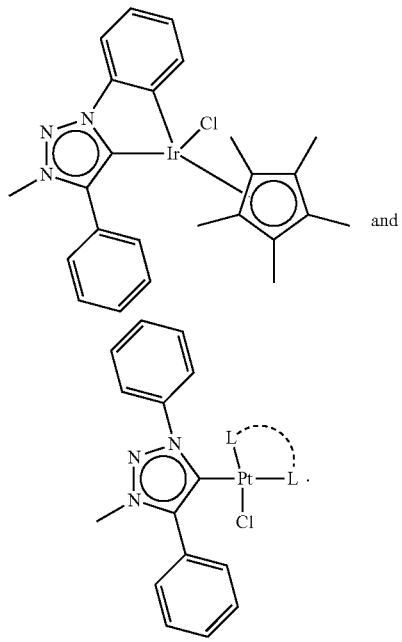

(L---L = COD)

No application for this metal complexes is reported.

D. G. Brown et al. (J. Am. Chem. Soc. 2013, 135, 1692) reported the synthesis of 1,2,3-triazolylidene carbene-based pincer ligands for the synthesis of ruthenium complexes for light harvesting complexes for application in dye-sensitized solar cells.

Even though there are already known Ir and Pt carbene complexes which are suitable for use in OLEDs, especially as light-emitting substances, it is desirable to provide more stable and/or more efficient compounds which are usable in industry.

SUMMARY OF THE INVENTION

It is therefore an object of the present invention to provide iridium and platinum complexes which are suitable for use in organic electronic devices. More particularly, the iridium and platinum complexes shall be suitable for use in OLEDs as emitters, matrix material, charge transport material, or charge blockers. The complexes shall be particularly suitable for color-tuning of the electroluminescence, which enables, for example, the production of full-color displays and white OLEDs. It is a further object of the present invention to provide corresponding complexes which can be used as a mixture with a host compound (matrix material) or as a pure layer as a light-emitting layer in OLEDs. More particularly, it is desirable to provide Ir and Pt transition metal complexes which exhibit a spectrum of properties improved over known Ir or Pt complexes, for example improved efficiencies, improved CIE color coordinates, suitable emission shape to enable the fabrication of white OLEDs with high CRI and/or improved lifetime/stability.

Surprisingly, it was found that these objects are achieved in accordance with the invention by metal-carbene complexes of the general formula

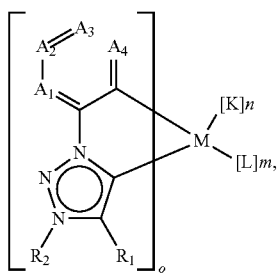

(I)

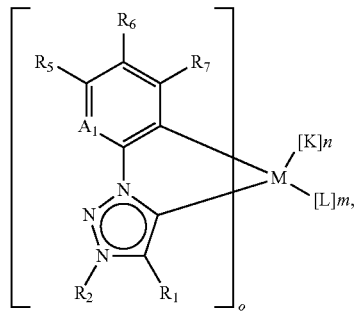

(II)

wherein M is Ir or Pt, $R_1$ and $R_2$ are independently of each other a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $A_1$, $A_2$, $A_3$ and $A_4$ are independently from each other $CR_3$ or N;

each $R_3$ is independently of each other H, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms; or a group with donor or acceptor action;

K and L are independently from each other a bidentate monoanionic ligand;

for M is Ir, o is 1, 2 or 3, m is 0, 1, or 2, n is 0, 1, or 2 and m+n+o=3 and for M is Pt, o is 1, or 2, m is 0, or 1, n is 0, or 1 and m+n+o=2.

The inventive metal-carbene complexes can be used in electronic devices, especially OLEDs (Organic Light-Emitting Diodes), for example, as emitter, matrix material, charge transport material and/or charge or exciton blocker.

The inventive metal-carbene complexes are generally notable for light emission in a wide range of the electromagnetic spectrum having a broad emission shape. This can be beneficial for the implementation in a 3-color white to achieve high color rendering indices.

The inventive metal-carbene complexes are therefore suitable with particular preference as emitter material in OLEDs.

The metal-carbene complex is preferably a metal-carbene complex of the general formula wherein $A_1$ is N, or $CR_4$, $R_4$, $R_5$, $R_6$ and $R_7$ are independently of each other H, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms; or a group with donor or acceptor action and $R_1$, $R_2$, M, K, L, n, m and o are as defined above.

K and L are bidentate monoanionic ligands. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and diarylphosphinoalkanols (diarylphosphinoalkoxide ligands). Examples of particularly preferred ligands K and L are given below.

In a particularly preferred embodiment the present invention is directed to metal-carbene complexes of the general formula

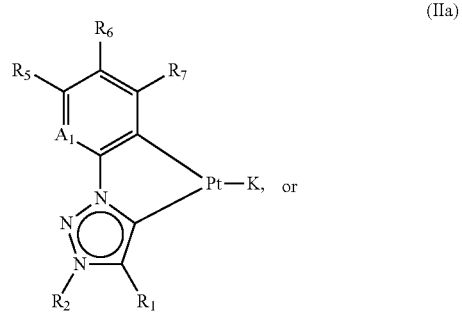

(IIa)

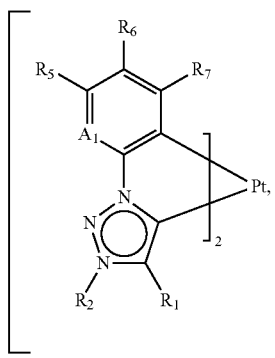

wherein K is a bidentate monoanionic ligand of formula

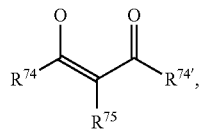

(A)

in which $R^{74}$ and $R^{74'}$ are in each case independently a linear or branched alkyl radical having 1 to 6 carbons atoms optionally bearing at least one functional group; substituted or unsubstituted cycloalkyl radical having 3 to 20 carbon atoms, substituted or unsubstituted aryl radical having 6 to 20 carbon atoms, preferably unsubstituted phenyl, 2,6-dialkylphenyl or 2,4,6-trialkylphenyl; substituted or unsubstituted heteroaryl radical having a total of 5 to 18 carbon atoms and/or heteroatoms, and
$R^{75}$ is hydrogen, a linear or branched alkyl radical having 1 to 6 carbon atoms, substituted or unsubstituted aryl radical having 6 to 20 carbon atoms;
$A_1$ is N, or $CR_4$,
$R_4$, $R_5$, $R_6$ and $R_7$ are independently of each other H, a linear or branched alkyl radical optionally interrupted by at least one heteroatom, optionally bearing at least one functional group and having 1 to 6 carbon atoms, substituted or unsubstituted cycloalkyl radical optionally interrupted by at least one heteroatom, optionally bearing at least one functional group and having 3 to 12 carbon atoms, substituted or unsubstituted aryl radical optionally interrupted by at least one heteroatom, optionally bearing at least one functional group and having 6 to 15 carbon atoms, substituted or unsubstituted heteroaryl radical optionally interrupted by at least one heteroatom, optionally bearing at least one functional group and having a total of 5 to 15 carbon atoms and/or heteroatoms; or a group with donor or acceptor action, selected from halogen radicals, $SiMe_3$, $SiPh_3$, OMe, $NO_2$, CN, NCO, NCS, $CF_3$, and
$R_1$ and $R_2$ are independently of each other a linear or branched alkyl radical optionally interrupted by at least one heteroatom, optionally bearing at least one functional group and having 1 to 6 carbon atoms, substituted or unsubstituted cycloalkyl radical optionally interrupted by at least one heteroatom, optionally bearing at least one functional group and having 3 to 12 carbon atoms, substituted or unsubstituted aryl radical, optionally bearing at least one functional group and having 6 to 15 carbon atoms, substituted or unsubstituted heteroaryl radical optionally interrupted by at least one heteroatom, optionally bearing at least one functional group and having a total of 5 to 15 carbon atoms and/or heteroatoms. Metal-carbene complexes of the general formula (IIa) are more preferred than Metal-carbene complexes of the general formula (IIb).

The alkyl radical having 1 to 6 carbons atoms $R^{74}$ and $R^{74'}$ is preferably selected from methyl, trifluoromethyl, ethyl, isopropyl, tert-butyl. The aryl radical having 6 to 20 carbon atoms is preferably selected from unsubstituted phenyl, 2,6-dialkylphenyl or 2,4,6-trialkylphenyl. The heteroaryl radical having a total of 5 to 18 carbon atoms and/or heteroatoms is preferably selected from thiophenyl and furanyl. The cycloalkyl radical having 3 to 20 carbon atoms is preferably selected from cyclopentyl, or cyclohexyl, which may optionally be substituted by a linear or branched alkyl radical having 1 to 6 carbon atoms, or phenyl.

Examples of particularly suitable compounds HK,

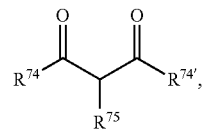

from which the ligands K are derived, include

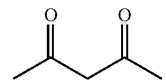

(2,4-pentanedione [acac]),

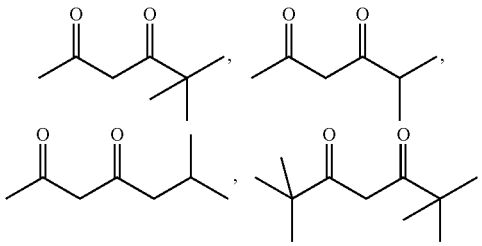

(2,2,6,6-tetramethyl-3,5-heptanedione [TMH]),

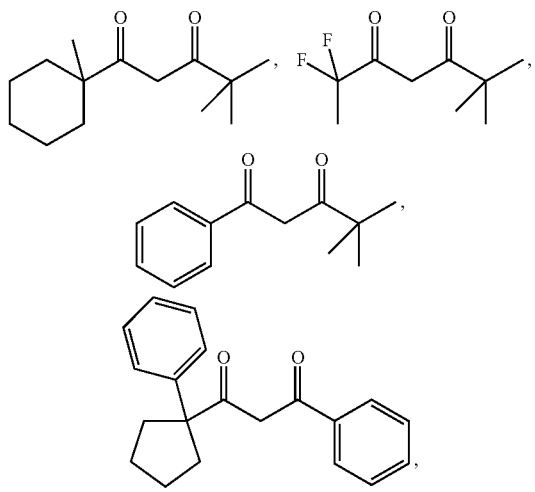

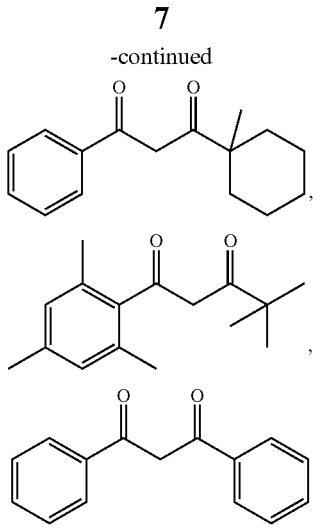

(1,3-diphenyl-1,3-propanedione [DI]),

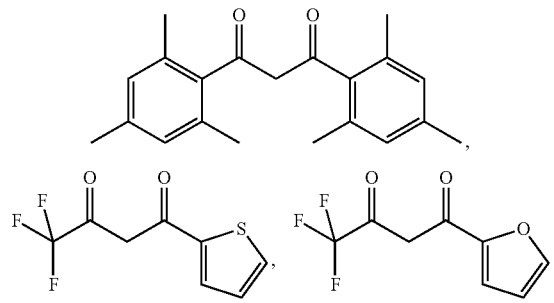

(4,4,4-trifluoro-1-(2-thienyl)-1,3-butanedione [TTFA]),

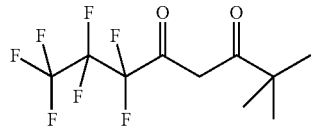 [SMILES: CC(C)(C)C(=O)CC(=O)C(F)(F)C(F)(F)C(F)(F)F]

(7,7-dimethyl-1,1,1,2,2,3,3-heptafluoro-4,6-octanedione [FOD]).

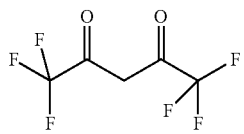 [SMILES: O=C(CC(=O)C(F)(F)F)C(F)(F)F]

(1,1,1,5,5,5-hexafluoro-2,4-pentanedione [F6acac]).

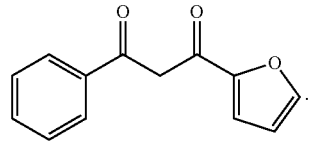

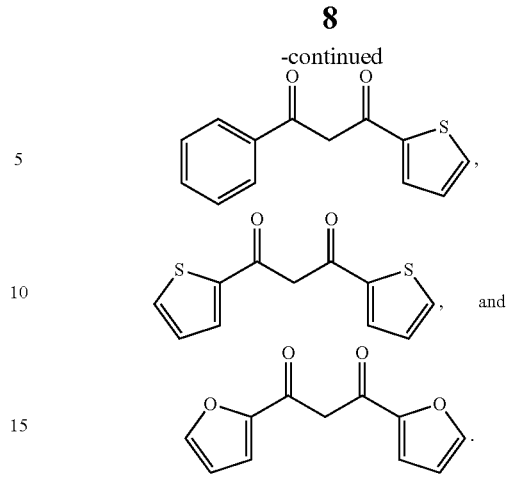

In a particularly preferred embodiment of the present invention K is selected from ligands of the formula

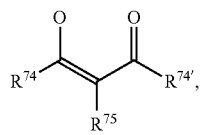

in which $R^{74}$ and $R^{74'}$ are methyl, ethyl, isopropyl, tert-butyl; phenyl, 2,6-dialkylphenyl or 2,4,6-trialkylphenyl; and $R^{75}$ is hydrogen.

In another particularly preferred embodiment the present invention is directed to metal-carbene complexes of the general formula

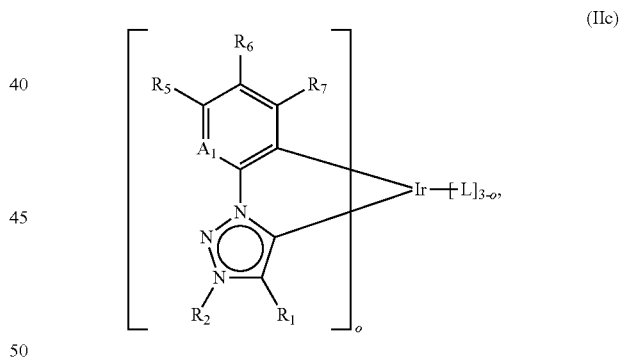

(IIc)

wherein
o is 1, 2, or 3,
L is a bidentate monoanionic ligand of formula

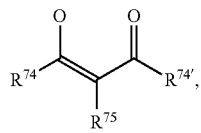

in which $R^{74}$ and $R^{74'}$ are in each case independently a linear or branched alkyl radical having 1 to 6 carbons atoms optionally bearing at least one functional group; substituted or unsubstituted cycloalkyl radical having 3 to 20 carbon atoms, substituted or unsubstituted aryl radical having 6 to 20 carbon atoms, preferably unsubstituted phenyl, 2,6-dialkylphenyl or 2,4,6-trialkylphenyl; substituted or unsubstituted heteroaryl radical having a total of 5 to 18 carbon atoms and/or heteroatoms, and $R^{75}$ is hydrogen, a linear or branched alkyl radical having 1 to 6 carbon atoms, substituted or unsubstituted aryl radical having 6 to 20 carbon atoms; or a ligand (X-37'), or (X-1) to (X-60) as defined in claim 4;

$A_1$ is N, or $CR_4$, $R_4$, $R_5$, $R_6$ and $R_7$ are independently of each other H, a linear or branched alkyl radical optionally interrupted by at least one heteroatom, optionally bearing at least one functional group and having 1 to 6 carbon atoms, substituted or unsubstituted cycloalkyl radical optionally interrupted by at least one heteroatom, optionally bearing at least one functional group and having 3 to 12 carbon atoms, substituted or unsubstituted aryl radical optionally interrupted by at least one heteroatom, optionally bearing at least one functional group and having 6 to 15 carbon atoms, substituted or unsubstituted heteroaryl radical optionally interrupted by at least one heteroatom, optionally bearing at least one functional group and having a total of 5 to 15 carbon atoms and/or heteroatoms; or a group with donor or acceptor action, selected from halogen radicals, $SiMe_3$, $SiPh_3$, OMe, $NO_2$, CN, NCO, NCS, $CF_3$, and $R_1$ and $R_2$ are independently of each other a linear or branched alkyl radical optionally interrupted by at least one heteroatom, optionally bearing at least one functional group and having 1 to 6 carbon atoms, substituted or unsubstituted cycloalkyl radical optionally interrupted by at least one heteroatom, optionally bearing at least one functional group and having 3 to 12 carbon atoms, substituted or unsubstituted aryl radical, optionally bearing at least one functional group and having 6 to 15 carbon atoms, substituted or unsubstituted heteroaryl radical optionally interrupted by at least one heteroatom, optionally bearing at least one functional group and having a total of 5 to 15 carbon atoms and/or heteroatoms.

Examples of particularly suitable compounds HL,

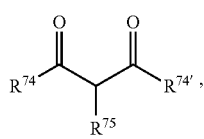

from which the ligands L are derived, include

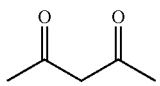

(2,4-pentanedione [acac]),

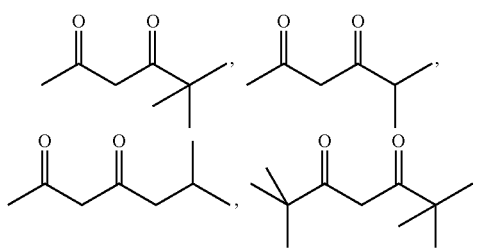

(2,2,6,6-tetramethyl-3,5-heptanedione [TMH]),

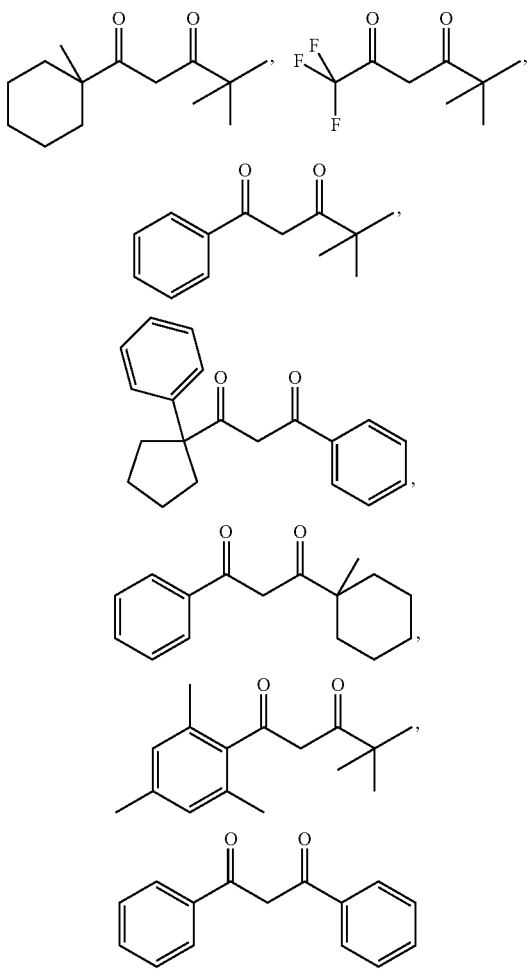

(1,3-diphenyl-1,3-propanedione [DI]),

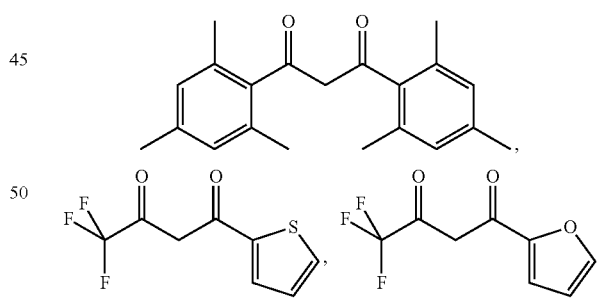

(4,4,4-trifluoro-1-(2-thienyl)-1,3-butanedione [TTFA]),

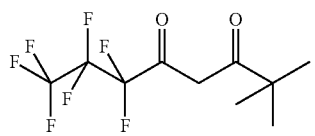 [SMILES: CC(C)(C)C(=O)CC(=O)C(F)(F)C(F)(F)C(F)(F)F]

(7,7-dimethyl-1,1,1,2,2,3,3-heptafluoro-4,6-octanedione [FOD]),

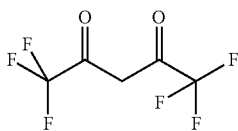 [SMILES: O=C(CC(=O)C(F)(F)F)C(F)(F)F]

(1,1,1,5,5,5-hexafluoro-2,4-pentanedione [F6acac]),

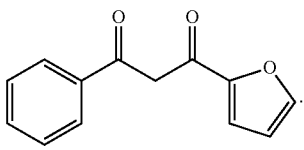

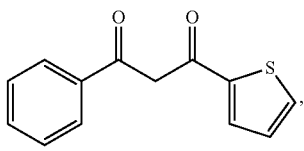

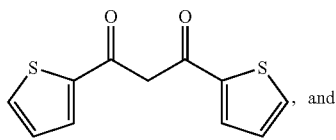, and

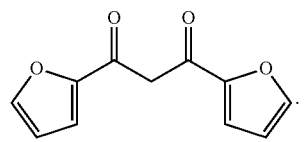.

In another particularly preferred embodiment the present invention is directed to metal-carbene complexes of the general formula (IIc), wherein L is a bidentate monoanionic ligand of formula (X-37'), or (X-1) to (X-60) as defined in claim 4.

In an even more preferred embodiment of the present invention L is selected from ligands of the formula

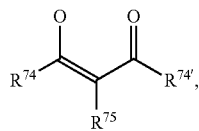

in which $R^{74}$ and $R^{74'}$ are methyl, ethyl, isopropyl, tert-butyl; phenyl, 2,6-dialkylphenyl or 2,4,6-trialkylphenyl; and $R^{75}$ is hydrogen.

In said embodiment metal-carbene complexes of the general formula

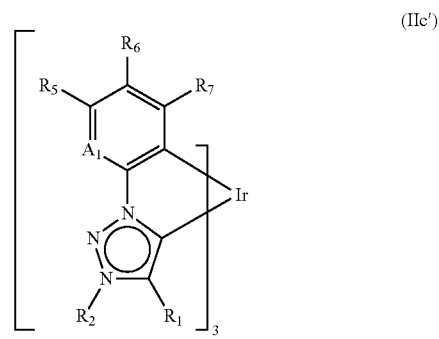

(IIc')

are even more preferred, wherein $R_1$, $R_2$, $R_5$, $R_6$, $R_7$ and $A_1$ are as defined above.

In the above formulae I, IIa, IIb, IIc and IIc' the substituents $R_1$, $R_2$, $R_5$, $R_6$, $R_7$ and $A_1$ have the following preferences:

$R_7$ is preferably hydrogen.

$A_1$ is preferably $CR_4$, wherein $R_4$ is hydrogen, a linear or branched alkyl radical having 1 to 6 carbon atoms, substituted or unsubstituted aryl radical having 6 to 15 carbon atoms, or a group with donor or acceptor action selected from CN, $CF_3$, $SiMe_3$, halogen radicals, preferably F. Most preferred $A_1$ is CH.

$R_5$ is preferably hydrogen, a linear or branched alkyl radical having 1 to 6 carbon atoms, substituted or unsubstituted aryl radical having 6 to 15 carbon atoms, or a group with donor or acceptor action selected from CN, $CF_3$, $SiMe_3$, halogen radicals, preferably F. Most preferred $R_5$ is hydrogen.

$R_6$ is preferably hydrogen, a linear or branched alkyl radical having 1 to 6 carbon atoms, substituted or unsubstituted aryl radical having 6 to 15 carbon atoms, or a group with donor or acceptor action selected from CN, $CF_3$, $SiMe_3$, halogen radicals, preferably F. Most preferred $R_6$ is hydrogen, F, or $CF_3$.

$R_1$ is preferably a linear or branched alkyl radical having 1 to 6 carbon atoms, a substituted or unsubstituted aryl radical having 6 to 20 carbon atoms, a substituted or unsubstituted heteroaryl radical having a total of 5 to 18 carbon atoms and/or heteroatoms. More preferred $R_1$ is

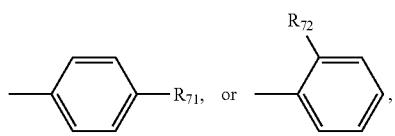

wherein $R^{71}$ is hydrogen, $C_1$-$C_4$alkyl, F, or $CF_3$ and $R^{72}$ is hydrogen, $C_1$-$C_4$alkyl, F, or $CF_3$. Most preferred $R_1$ is

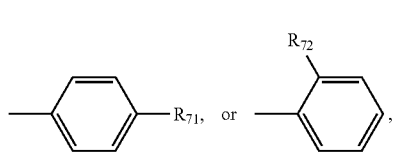

wherein $R^{71}$ is hydrogen, $CH_3$, F, or $CF_3$ and $R^{72}$ is $CH_3$, F, or $CF_3$.

$R_2$ is preferably a linear or branched alkyl radical having 1 to 6 carbons atoms, or a unsubstituted aryl radical having 6 to 15 carbon atoms. More preferred $R_2$ is

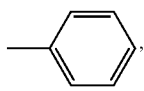

or $C_1-C_8$alkyl. Most preferred $R_2$ is

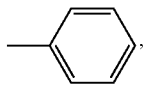

or $C_1-C_4$alkyl, such as methyl, or isopropyl.

In a particularly preferred embodiment the present invention is directed to metal-carbene complexes of formulae I, IIa, IIb, IIc and IIc', wherein
$R_1$ is

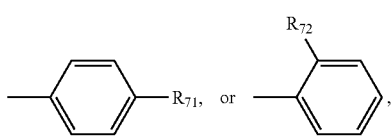

wherein $R^{71}$ is hydrogen, $CH_3$, F, or $CF_3$ and $R^{72}$ is $CH_3$, F, or $CF_3$.
$R_2$ is

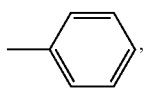

or $C_1-C_4$alkyl, such as methyl, or isopropyl.
$A_1$ is CH,
$R_5$ is hydrogen,
$R_6$ is hydrogen, F, or $CF_3$.
$R_7$ is hydrogen.

Examples of suitable compounds are metal-carbene complexes EM-1 to EM-55 as shown in claim 12.

DETAILED DESCRIPTION OF THE INVENTION

Ligands suitable for the synthesis of inventive complexes can be synthesized according to the following literature known procedures:

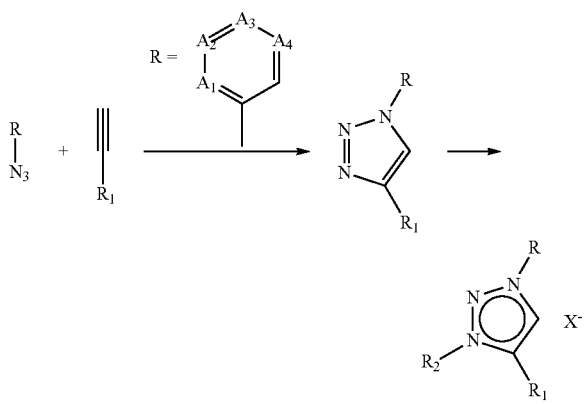

Starting materials are easily available and R and $R_1$ can be selected from a wide variety of moieties, such as aryl, alkyl and heterocycles, and several different cyclization conditions are available. Reference is made, for example, to J. D. Crowley et al., Polyhedron, 2010, 70-83; G. Guisado-Barrios et al., Angew. Chem. Int. Ed. 2010, 49, 4759-4762; S. Diez-González et al., Angew. Chem. Int. Ed. 2008, 47, 8881-8884. Alkylation with $R_2$ can be achieved by reaction with alkyl halides. Reference is made, for example, to B. Schulze, Org. Lett. 2010, 12, 2710-2713.

Interesting especially for $R_1$ moieties with low molecular weight (e.g. $R_1$=iPr) synthesis starting from the respective carboxylic acids can be advantageous.

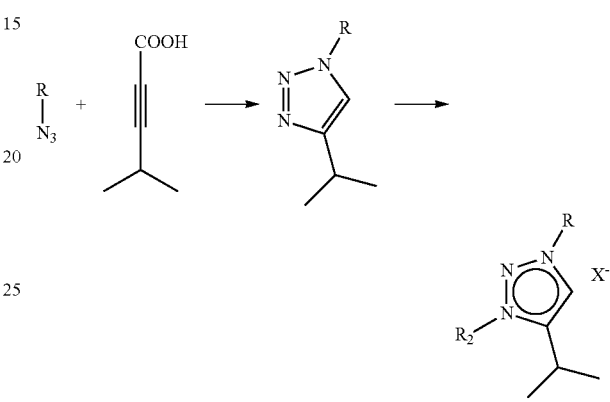

Conditions for this procedure are described, for example, in A. Kolarovic et al., J. Org. Chem. 2011, 76, 2613-2618.

To access ligands with $R_2$=aryl, an alternative synthesis can be used:

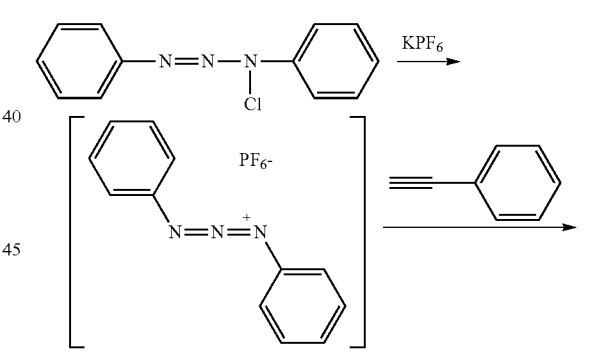

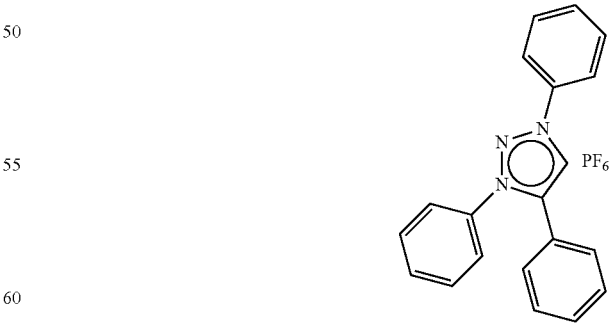

Also here a wide variety of ligands is accessible by choosing the respective starting materials. Reference is made, for example, to W. Wirschun et al., J. Chem. Soc., Perkin Trans. 1, 1998, 1755-1761; W. Wirschun et al., Synthesis 1997, 233-241.

A process for preparing the metal-carbene complexes according to the present invention involves contacting suitable compounds comprising M with compounds of the general formula

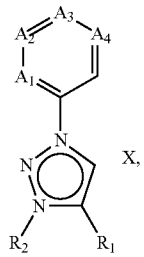

(IV)

wherein $A_1$ to $A_4$, $R_1$ and $R_2$ are each as defined above and X is F, Cl, Br, I, $PF_6$, or $BF_4$.

Customary processes involve, for example, the deprotonation of the triazole ligand precursors of formula (IV) and subsequent reaction, generally in situ, with suitable Pt/Ir-comprising metal compounds and optionally precursors of ligands K and/or L.

The process for preparing the inventive metal-carbene complexes is illustrated below in more detail on basis of inventive platinum-carbene complexes of formula I, wherein M is Pt and L is a ligand of formula

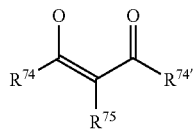

as well as homoleptic Iridium complexes, but is not limited thereto.

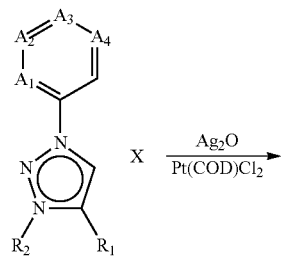

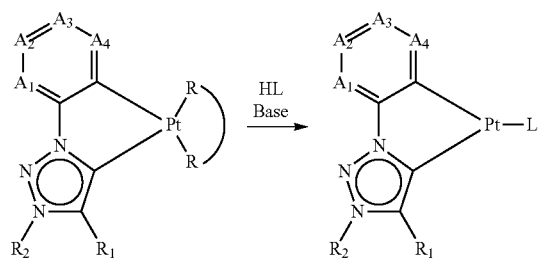

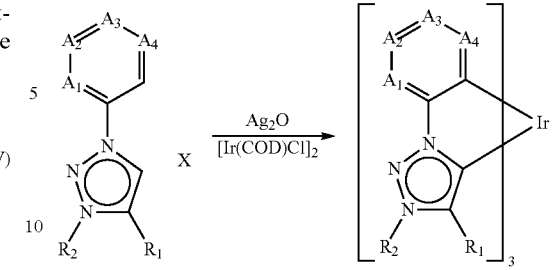

The process comprises the following steps (R—R=COD):
(i) the deprotonation of the triazole ligand precursors of formula (IV);
(ii) subsequent reaction with suitable Pt-comprising metal compounds; and
(iii) reaction of the intermediate obtained in step ii) with HL in the presence of a base.

Deprotonation in step i) can be accomplished by basic compounds known to those skilled in the art, for example basic metallates, basic metal acetates, acetylacetonates or alkoxylates, or bases such as $KO^tBu$, $NaO^tBu$, $LiO^tBu$, NaH, silylamides and phosphazene bases. Preference is given to deprotonating with $Ag_2O$.

The deprotonation is preferably effected in a solvent. Suitable solvents are known per se to those skilled in the art and are preferably selected from the group consisting of aromatic and aliphatic solvents, ethers, alcohols, esters, amides, ketones, nitriles, halogenated compounds and mixtures thereof. A particularly preferred solvent is dichloromethane.

The reaction is effected generally at a temperature of 0 to 50° C. The reaction time depends on the desired carbene complex and is generally 1 to 80 hours, preferably 2 to 70 hours, more preferably 10 to 60 hours.

Then the deprotonated triazole crben ligand precursors of formula (IV) are reacted with suitable ft/Pt-comprising metal compounds.

Heteroleptic inventive Ir complexes consisting of 1 or 2 triazolo carbene ligands are accessible by published procedures, e.g. WO11051404A1 and WO11073149A1

In the context of the present invention, the terms aryl radical, unit or group, heteroaryl radical, unit or group, alkyl radical, unit or group, cycloalkyl radical, unit or group, and groups with donor or acceptor action are each defined as follows—unless stated otherwise:

Aryl radicals or substituted or unsubstituted aryl radicals having 6 to 30 carbon atoms ($C_6$-$C_{30}$-aryl radicals) refer in the present invention to radicals which are derived from monocyclic, bicyclic or tricyclic aromatics which do not comprise any ring heteroatoms. When the systems are not monocyclic systems, the term "aryl" for the second ring also includes the saturated form (perhydro form) or the partly unsaturated form (for example the dihydro form or tetrahydro form), provided that the particular forms are known and stable. This means that the term "aryl" in the present invention encompasses, for example, also bicyclic or tricyclic radicals in which either both or all three radicals are aromatic, and bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to $C_6$-$C_{10}$-aryl radicals, for example phenyl or naphthyl, very particular preference to $C_6$-aryl radicals, for example phenyl.

The aryl radicals or $C_6$-$C_{30}$-aryl radicals may be unsubstituted or substituted by one or more further radicals. Suitable further radicals are selected from the group consisting of $C_1$-$C_{20}$-alkyl, $C_6$-$C_{30}$-aryl and substituents with donor or acceptor action, suitable substituents with donor or acceptor action are specified below. The $C_6$-$C_{30}$-aryl radicals are preferably unsubstituted or substituted by one or more $C_1$-$C_{20}$-alkyl groups, $C_1$-$C_{20}$-alkoxy groups, CN, $CF_3$, F or amino groups ($NR^{62}R^{63}$ where suitable $R^{62}$ and $R^{63}$ radicals are preferably each independently substituted or unsubstituted alkyl or substituted or unsubstituted phenyl, suitable substituents having been specified above).

Heteroaryl radicals or substituted or unsubstituted heteroaryl radicals having a total of 5 to 18 carbon atoms and/or heteroatoms are understood to mean monocyclic, bicyclic or tricyclic heteroaromatics, some of which can be derived from the aforementioned aryl, in which at least one carbon atom in the aryl base structure has been replaced by a heteroatom. Preferred heteroatoms are N, O and S. The heteroaryl radicals more preferably have 5 to 13 ring atoms. The base structure of the heteroaryl radicals is especially preferably selected from systems such as pyridine and five-membered heteroaromatics such as thiophene, pyrrole, imidazole, thiazole, oxazole or furan. These base structures may optionally be fused to one or two six-membered aromatic radicals. Suitable fused heteroaromatics are carbazolyl, benzimidazolyl, benzofuryl, benzothiazolyl, benzoxazolyl, dibenzofuryl or dibenzothiophenyl.

The base structure may be substituted at one, more than one or all substitutable positions, suitable substituents being the same as those already specified under the definition of $C_6$-$C_{30}$-aryl. However, the heteroaryl radicals are preferably unsubstituted. Suitable heteroaryl radicals are, for example, pyridin-2-yl, pyridin-3-yl, pyridin-4-yl, thiophen-2-yl, thiophen-3-yl, pyrrol-2-yl, pyrrol-3-yl, furan-2-yl, furan-3-yl, thiazol-2-yl, oxazol-2-yl and imidazol-2-yl, and the corresponding benzofused radicals, especially carbazolyl, benzimidazolyl, benzofuryl, benzothiazolyl, benzoxazolyl, dibenzofuryl or dibenzothiophenyl.

An alkyl radical in the context of the present application is a linear or branched alkyl radical optionally bearing at least one functional group, optionally interrupted by at least one heteroatom and having 1 to 20 carbon atoms. Preference is given to $C_1$- to $C_{10}$-alkyl radicals, particular preference to $C_1$- to $C_6$-alkyl radicals. In addition, the alkyl radicals may be substituted by one or more functional groups, preferably selected from the group consisting of $C_1$-$C_{20}$-alkyl, $C_1$-$C_{20}$-alkoxy, halogen, preferably F, $C_1$-$C_{20}$-haloalkyl, e.g. $CF_3$, and $C_6$-$C_{30}$-aryl which may in turn be substituted or unsubstituted. Suitable aryl substituents and suitable alkoxy and halogen substituents are specified above and below. Examples of suitable alkyl groups are methyl, ethyl, propyl, butyl, pentyl, hexyl, heptyl and octyl, and also $C_1$-$C_{20}$-alkyl-, $C_1$-$C_{20}$-haloalkyl-, $C_1$-$C_{20}$-alkoxy- and/or halogen-substituted, especially F-substituted, derivatives of the alkyl groups mentioned, for example $CF_3$. This comprises both the n-isomers of the radicals mentioned and branched isomers such as isopropyl, isobutyl, isopentyl, sec-butyl, tert-butyl, neopentyl, 3,3-dimethylbutyl, 3-ethylhexyl, etc. Preferred alkyl groups are methyl, ethyl, isopropyl, tert-butyl and $CF_3$.

A cycloalkyl radical or a substituted or unsubstituted cycloalkyl radical having 3 to 20 carbon atoms is understood in the context of the present application to mean a substituted or unsubstituted $C_3$-$C_{20}$-cycloalkyl radical. Preferred are cycloalkyl radicals having 5 to 20, more preferably 5 to 10 and most preferably 5 to 8 carbon atoms in the base structure (ring) to understand. Suitable substituents are the substituents mentioned for the alkyl groups. Examples of suitable cycloalkyl groups, which may be unsubstituted or substituted by the radicals mentioned above for the alkyl groups, are cyclopentyl, cyclohexyl, cycloheptyl, cyclooctyl, cyclononyl and cyclodecyl. They may also be polycyclic ring systems such as decalinyl, norbornyl, bornanyl or adamantyl.

Suitable alkoxy radicals derive correspondingly from the aforementioned alkyl radicals. Examples here include $OCH_3$, $OC_2H_5$, $OC_3H_7$, $OC_4H_9$ and $OC_8H_{17}$, and also $SCH_3$, $SC_2H_5$, $SC_3H_7$, $SC_4H_9$ and $SC_8H_{17}$. In this context, $C_3H_7$, $C_4H_9$ and $C_8H_{17}$ comprise both the n-isomers and branched isomers such as isopropyl, isobutyl, sec-butyl, tert-butyl and 2-ethylhexyl. Particularly preferred alkoxy or alkylthio groups are methoxy, ethoxy, n-octyloxy, 2-ethylhexyloxy and $SCH_3$.

Suitable halogen radicals or halogen substituents in the context of the present application are fluorine, chlorine, bromine and iodine, preferably fluorine, chlorine and bromine, more preferably fluorine and chlorine, most preferably fluorine.

In the context of the present application, groups with donor or acceptor action are understood to mean the following groups:
$C_1$-$C_{20}$-alkoxy, $C_6$-$C_{30}$-aryloxy, $C_1$-$C_{20}$-alkylthio, $C_6$-$C_{30}$-arylthio, $SiR^{64}R^{65}R^{66}$, halogen radicals, halogenated $C_1$-$C_{20}$-alkyl radicals, carbonyl ($—CO(R^{64})$), carbonylthio ($—C{=}O(SR^{64})$), carbonyloxy ($—C{=}O(OR^{64})$), oxycarbonyl ($—OC{=}O(R^{64})$), thiocarbonyl ($—SC{=}O(R^{64})$), amino ($—NR^{64}R^{65}$), OH, pseudohalogen radicals, amido ($—C{=}O$ $(NR^{64}R^{65})$), $—NR^{64}C{=}O(R^{65})$, phosphonate ($—P(O)$ $(OR^{64})_2$), phosphate ($—OP(O)$ $(OR^{64})_2$), phosphine ($—PR^{64}R^{65}$), phosphine oxide ($—P(O)R^{64}2$), sulfate ($—OS$ $(O)_2OR^{64}$), sulfoxide ($—S(O)R^{64}$), sulfonate ($—S(O)_2OR^{64}$), sulfonyl ($—S(O)_2R^{64}$), sulfonamide ($—S$ $(O)_2NR^{64}R^{65}$), $NO_2$, boronic esters ($—OB(OR^{64})_2$), imino ($—C{=}NR^{64}R^{65}$), borane radicals, stannate radicals, hydrazine radicals, hydrazone radicals, oxime radicals, nitroso groups, diazo groups, vinyl groups, sulfoximines, alanes, germanes, boroxines and borazines.

Preferred substituents with donor or acceptor action are selected from the group consisting of: $C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{64}R^{65}R^{66}$, where $R^{64}$, $R^{65}$ and $R^{66}$ are preferably each independently substituted or unsubstituted alkyl or substituted or unsubstituted phenyl, suitable substituents having been specified above; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino; OH, pseudohalogen radicals, preferably CN, SCN or OCN, more preferably CN, $—C(O)OC_1$-$C_4$-alkyl, preferably $—C(O)OMe$, $P(O)R_2$, preferably $P(O)Ph_2$, and $SO_2R_2$, preferably $SO_2Ph$.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{64}R^{65}R^{66}$, where suitable $R^{64}$, $R^{65}$ and $R^{66}$ radicals have been specified above, diphenylamino, $—C(O)OC_1$-$C_4$-alkyl, preferably $—C(O)OMe$, $P(O)Ph_2$ and $SO_2Ph$.

The aforementioned groups with donor or acceptor action are not intended to rule out the possibility that further radicals and groups among those specified above may also have donor or acceptor action. For example, the aforementioned heteroaryl radicals are likewise groups with donor or acceptor action, and the $C_1$-$C_{20}$-alkyl radicals are groups with donor action.

The inventive metal-carbene complexes can be used in electronic devices, for example organic electronic devices selected from switching elements such as organic light-emitting diodes (OLEDs), organic photovoltaic cells (OPVs), organic field-effect transistors (OFETs) and light-emitting electrochemical cells (LEECs), preference being given to using the metal-carbene complexes of the formula (I) in OLEDs.

In a preferred embodiment, the organic electronic device is an OLED comprising a light-emitting layer comprising at least one inventive metal-carbene complex.

The aforementioned inventive metal-carbene complexes and mixtures thereof are outstandingly suitable as emitter molecules in organic light-emitting diodes (OLEDs). Variations in the ligands make it possible to provide corresponding complexes which exhibit electroluminescence in a wide range of the electromagnetic spectrum. The inventive metal-carbene complexes are therefore outstandingly suitable as emitter substances and it is thus possible, with the aid of the inventive complexes as emitter substances, to provide industrially usable OLEDs.

In addition, the inventive metal-carbene complexes can be used as matrix material, charge transport material, especially hole transport material, and/or charge blocker.

The inventive metal-carbene complexes are preferably used as an emitter and/or charge transport material and/or matrix material, more preferably as an emitter.

Particular properties of the inventive metal-carbene complexes are particularly good efficiencies, good CIE color loci and long lifetimes when used in OLEDs.

The present application therefore further provides an OLED comprising at least one inventive metal-carbene complex. The inventive metal-carbene complex is used in the OLED preferably as an emitter, matrix material, charge transport material, especially hole transport material, and/or charge blocker, more preferably as an emitter and/or hole transport material, most preferably as an emitter.

The present application also provides for the use of the inventive metal-carbene complexes in OLEDs, preferably as an emitter, matrix material, charge transport material, especially hole transport material, and/or charge blocker, more preferably as an emitter and/or hole transport material, most preferably as an emitter.

Organic light-emitting diodes are in principle formed from a plurality of layers, e.g.:
(a) an anode,
(b) optionally a hole injection layer,
(c) optionally a hole transport layer,
(d) optionally an exciton blocking layer
(e) a light-emitting layer, comprising
(f) optionally a hole/exciton blocking layer
(g) optionally an electron transport layer,
(h) optionally an electron injection layer, and
(i) a cathode.

It is, however, also possible that the OLED does not have all of the layers mentioned; for example, an OLED comprising layers (a) (anode), (e) (light-emitting layer) and (i) (cathode) is likewise suitable, in which case the functions of layers (c) (hole-transport layer) and (g) (electron-transport layer) are assumed by the adjoining layers. OLEDs having layers (a), (c), (e), (g) and (i) or (a), (c), (e) and (i) or layers (a), (e), (g) and (i) are likewise suitable.

The inventive metal-carbene complexes are preferably used as emitter molecules and/or matrix materials in the light-emitting layer (e). The inventive metal-carbene complexes may—in addition to use as emitter molecules and/or matrix materials in the light-emitting layer (e) or instead of use in the light-emitting layer—also be used as a charge transport material in the hole-transport layer (c) or in the electron-transport layer (g) and/or as a charge blocker, preference being given to use as a charge transport material in the hole-transport layer (c) (hole transport material).

The present application therefore further provides a light-emitting layer comprising at least one of the inventive metal-carbene complexes, preferably as emitter material and/or matrix material, more preferably as emitter material. Preferred inventive metal-carbene complexes have already been specified above.

In a further embodiment, the present invention relates to a light-emitting layer consisting of at least one inventive metal-carbene complex.

The inventive metal-carbene complexes used in accordance with the invention may be present in the light-emitting layer in substance, i.e. without further additions. However, it is also possible that, in addition to the dinuclear metal-carbene complexes used in accordance with the invention, further compounds are present in the light-emitting layer. In addition, a diluent material (matrix material) may be used. This diluent material may be a polymer, for example poly (N-vinylcarbazole) or polysilane. The diluent material may, however, likewise be a small molecule, for example 4,4'-N, N'-dicarbazolebiphenyl (CDP) or tertiary aromatic amines. When a diluent material is used, the proportion of the inventive metal-carbene complexes in the light-emitting layer is generally less than 40% by weight, preferably 3 to 30% by weight. The inventive metal-carbene complexes are preferably used in a matrix. The light-emitting layer thus preferably comprises at least one inventive metal-carbene complex and at least one matrix material.

Suitable matrix materials are in principle the materials specified hereinafter as hole and electron transport materials, and also carben complexes, for example, the inventive metal-carbene complexes, or the carbene complexes mentioned in WO 2005/019373. Particularly suitable are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and the matrix materials specified in the following applications: WO2008/034758, WO2009/003919.

Further suitable matrix materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co)polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709, WO2014/009317 (EP12175635.7), PCT/EP2013/069403 (EP12185230.5) and PCT/EP2013/073120 (EP12191408.9; in particular page 25 to 29 of EP12191408.9).

In a particularly preferred embodiment, one or more compounds of the general formula (X) specified hereinafter are used as matrix material.

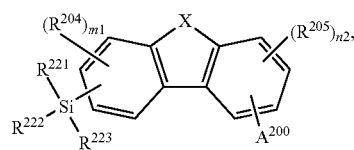

(X)

wherein
X is NR*, S, O or PR*;
R* is aryl, heteroaryl, alkyl, cycloalkyl, or heterocycloalkyl;
$A^{200}$ is $-NR^{206}R^{207}$, $-P(O)R^{208}R^{209}$, $-PR^{210}R^{211}$, $-S(O)_2R^{212}$, $-S(O)R^{213}$, $-SR^{214}$, or $-OR^{215}$;
$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl;
$R^{204}$ and $R^{205}$ are independently of each other alkyl, cycloalkyl, heterocycloalkyl, aryl, heteroaryl, a group $A^1$, or a group having donor, or acceptor characteristics;

n2 and m1 are independently of each other 0, 1, 2, or 3;
$R^{206}$, $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and
$R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocycloalkyl.

Compounds of formula (X) and their preparation processes, such as, for example,

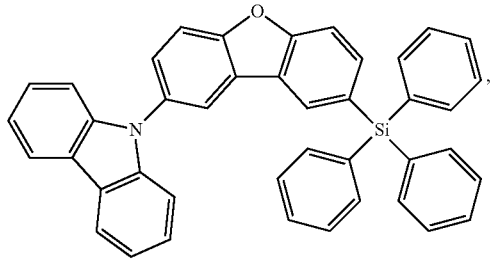

(SH-4)

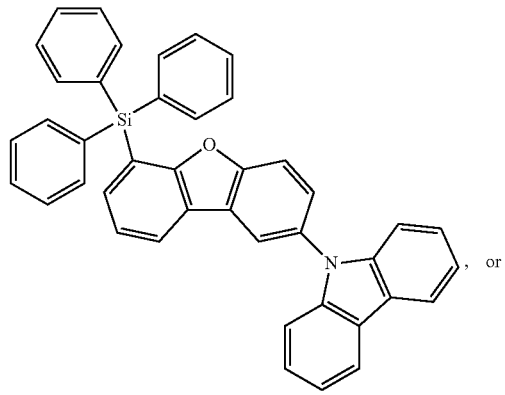

(SH-5)

, or

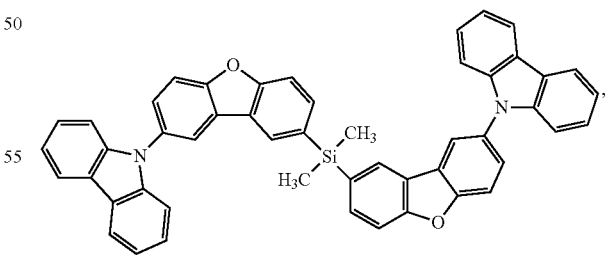

(SH-6)

are described in WO 2010/079051 A1 (in particular pages on 19 to 26 and in tables on pages 27 to 34, pages 35 to 37 and pages 42 to 43).

Additional host materials on basis of dibenzofurane are, for example, described in US 2009066226, EP1 885 818 B1, EP 1 970 976, EP 1 998 388 and EP 2 034 538. Examples of particularly preferred host materials are shown below:

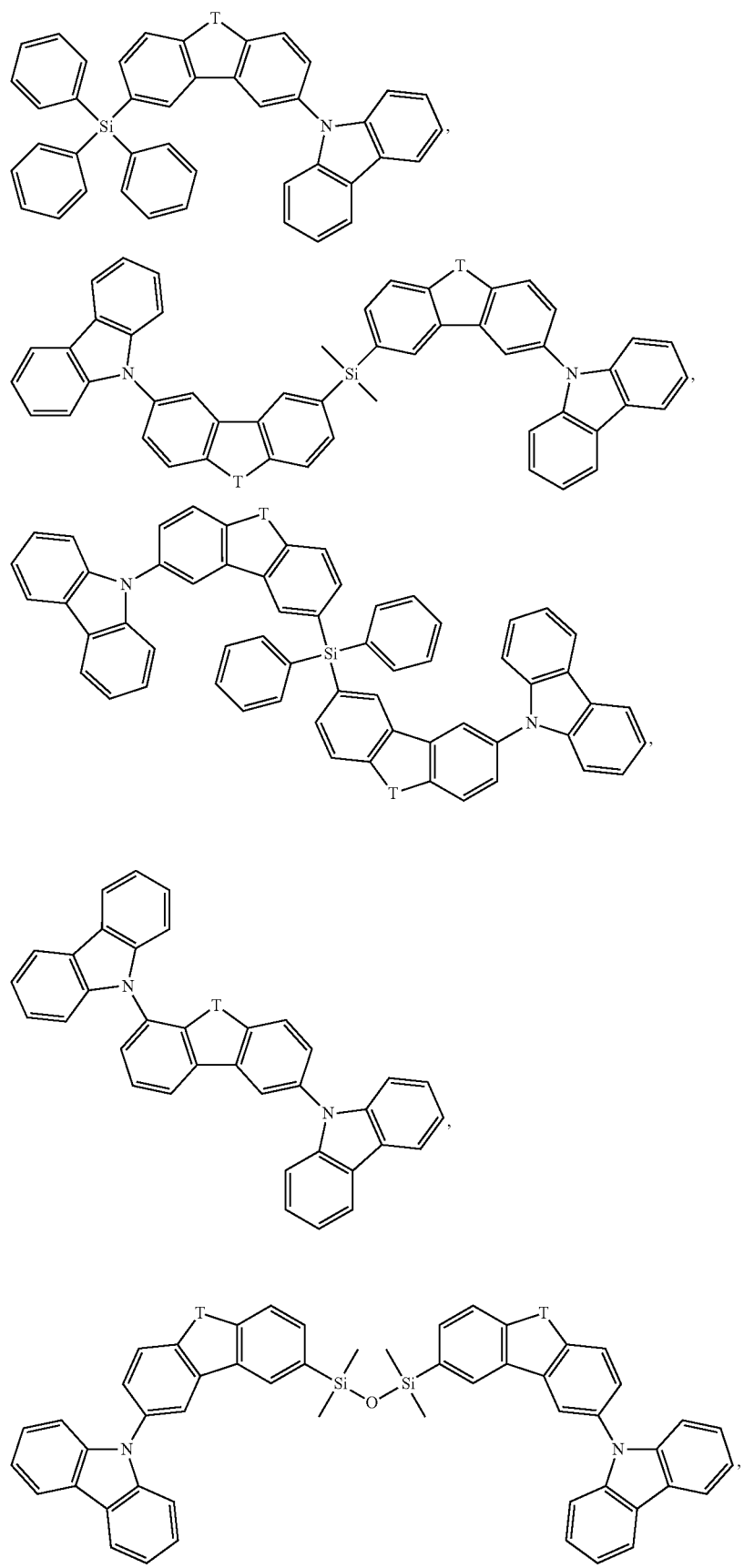

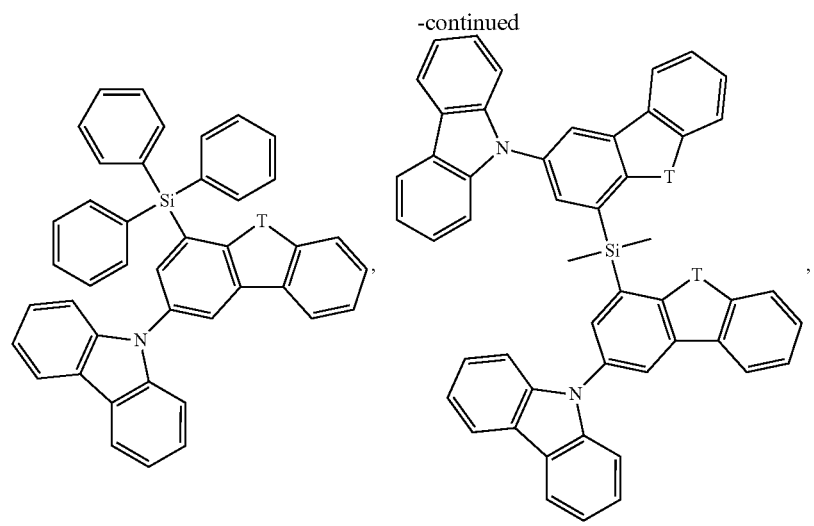
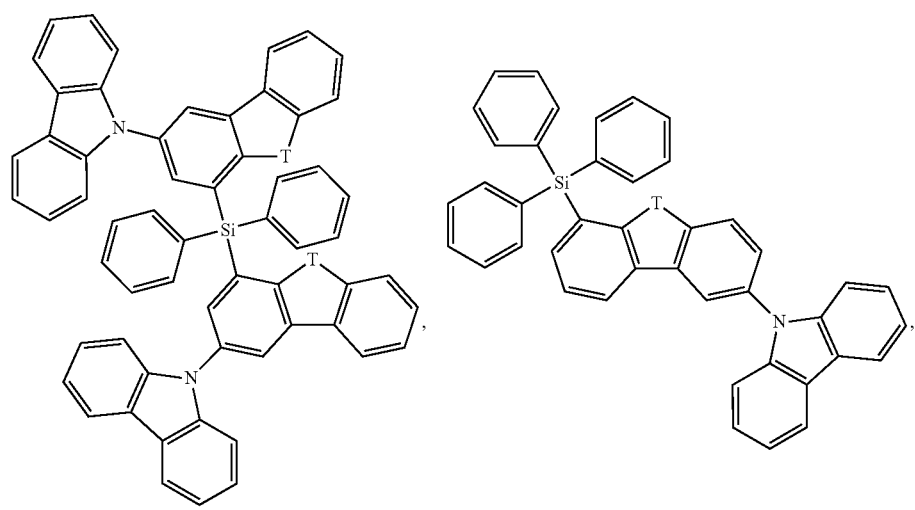
especially
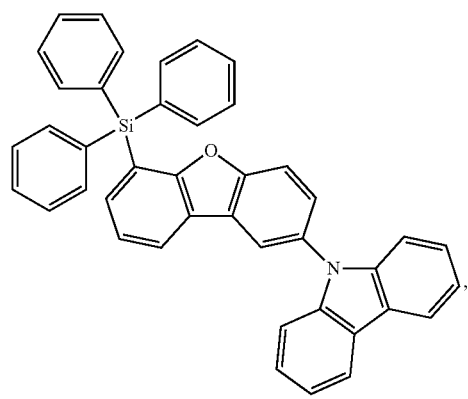

-continued
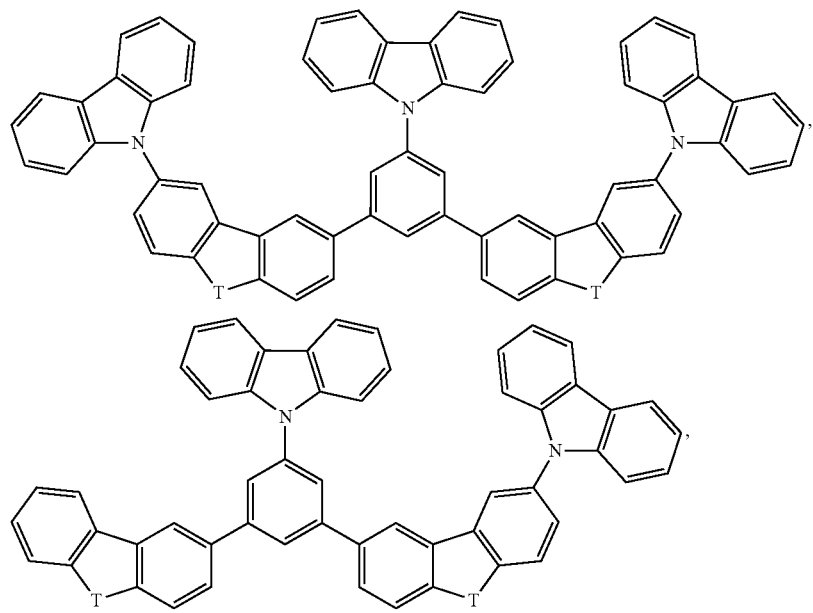
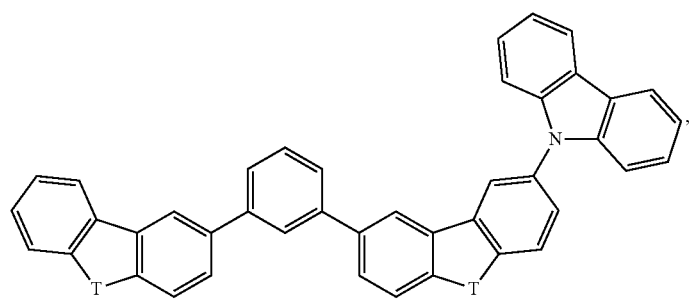
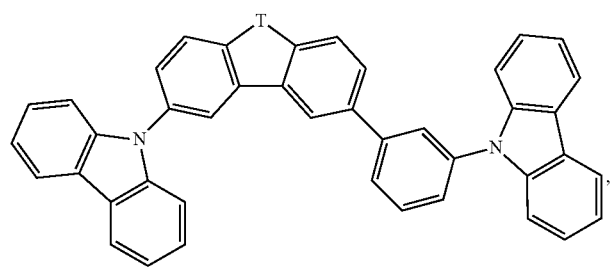
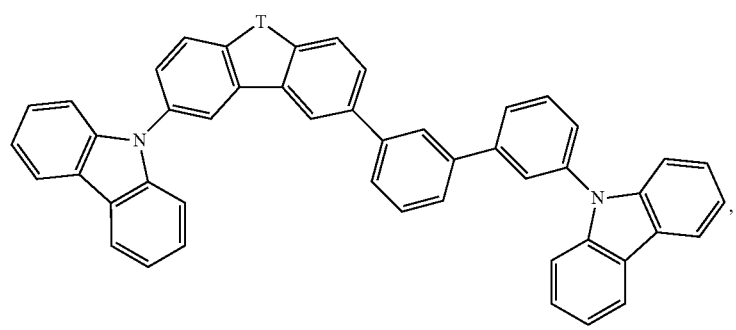

-continued
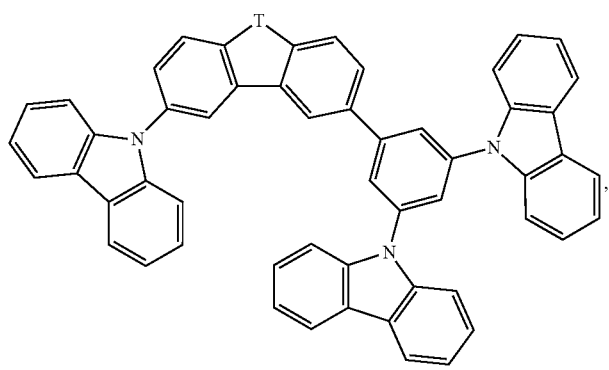
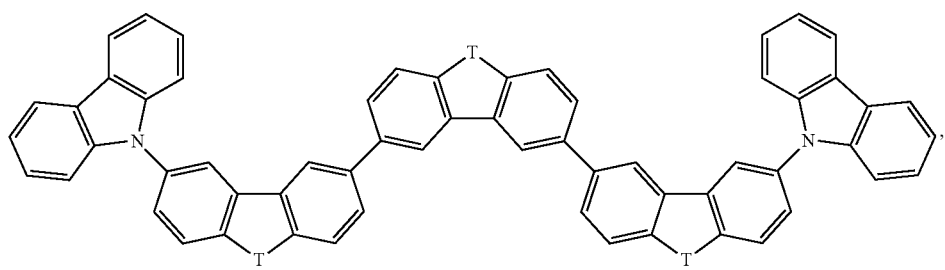
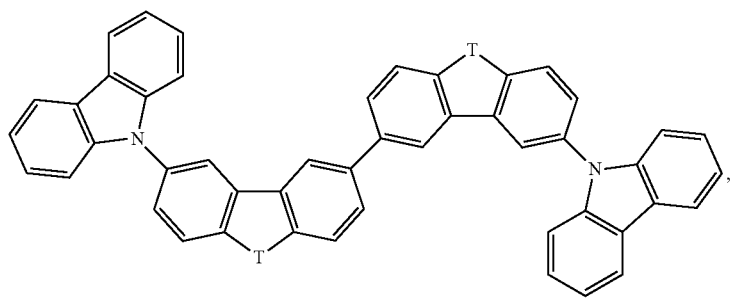
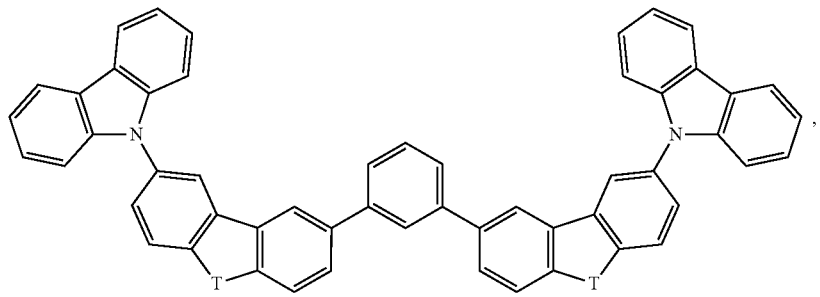
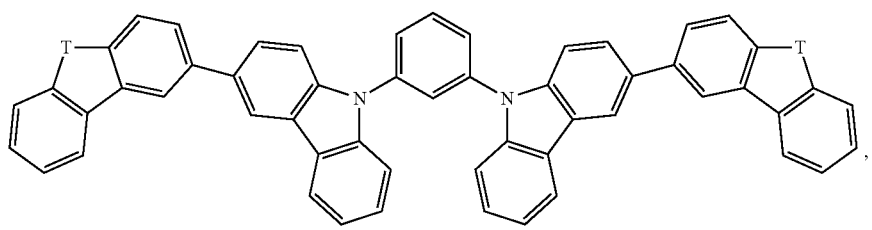

-continued
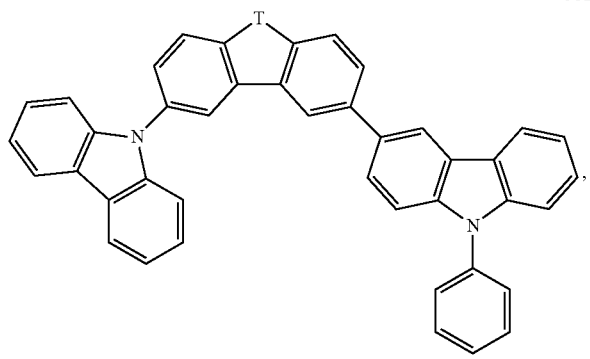
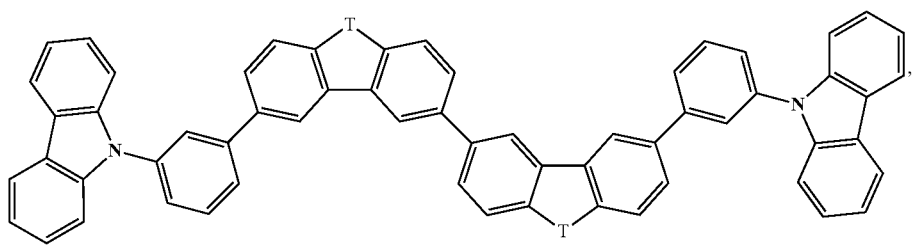
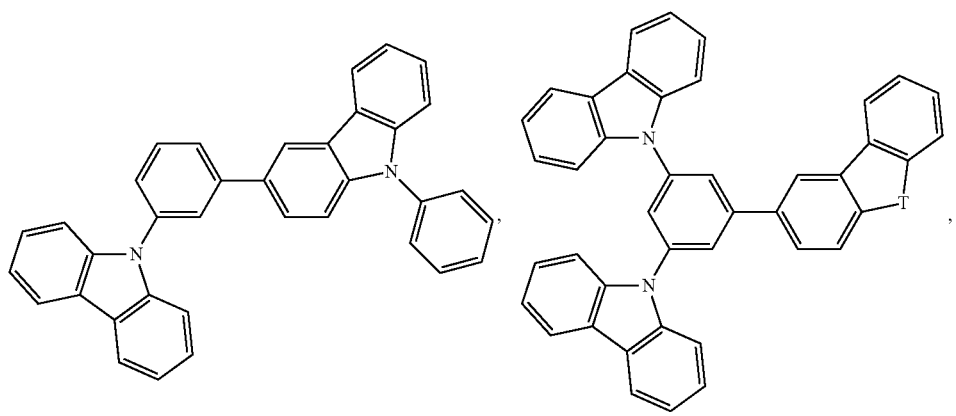
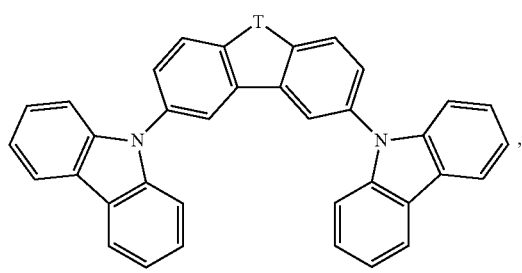
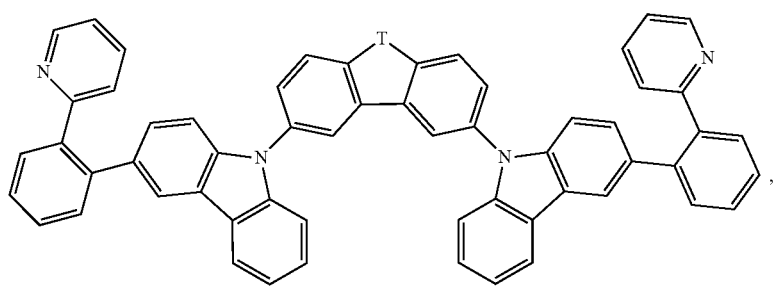

-continued
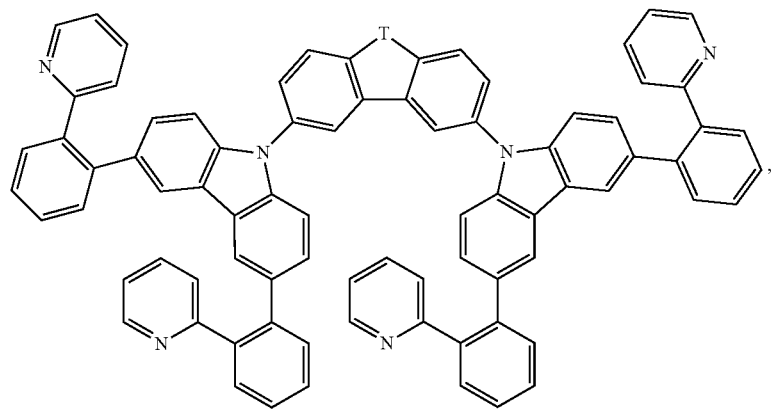
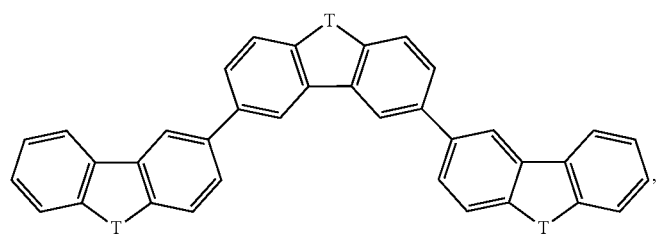
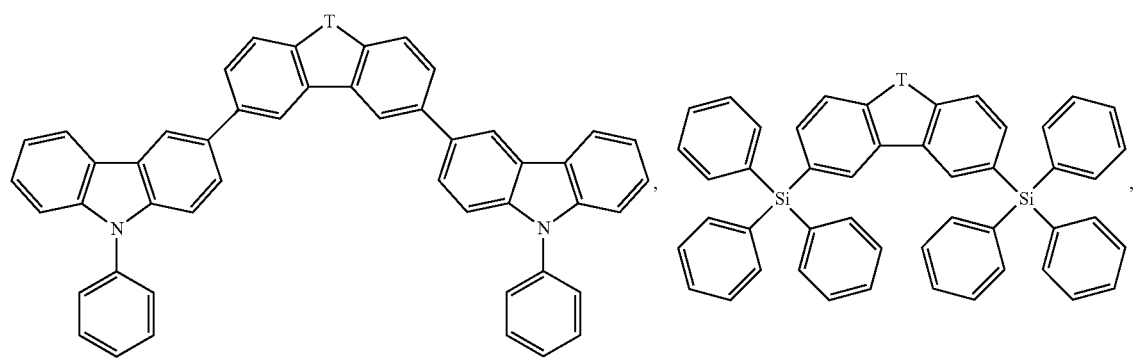
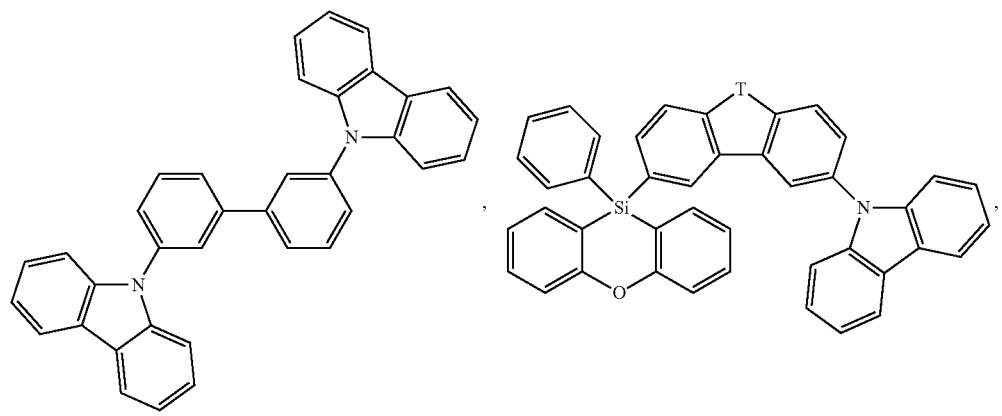

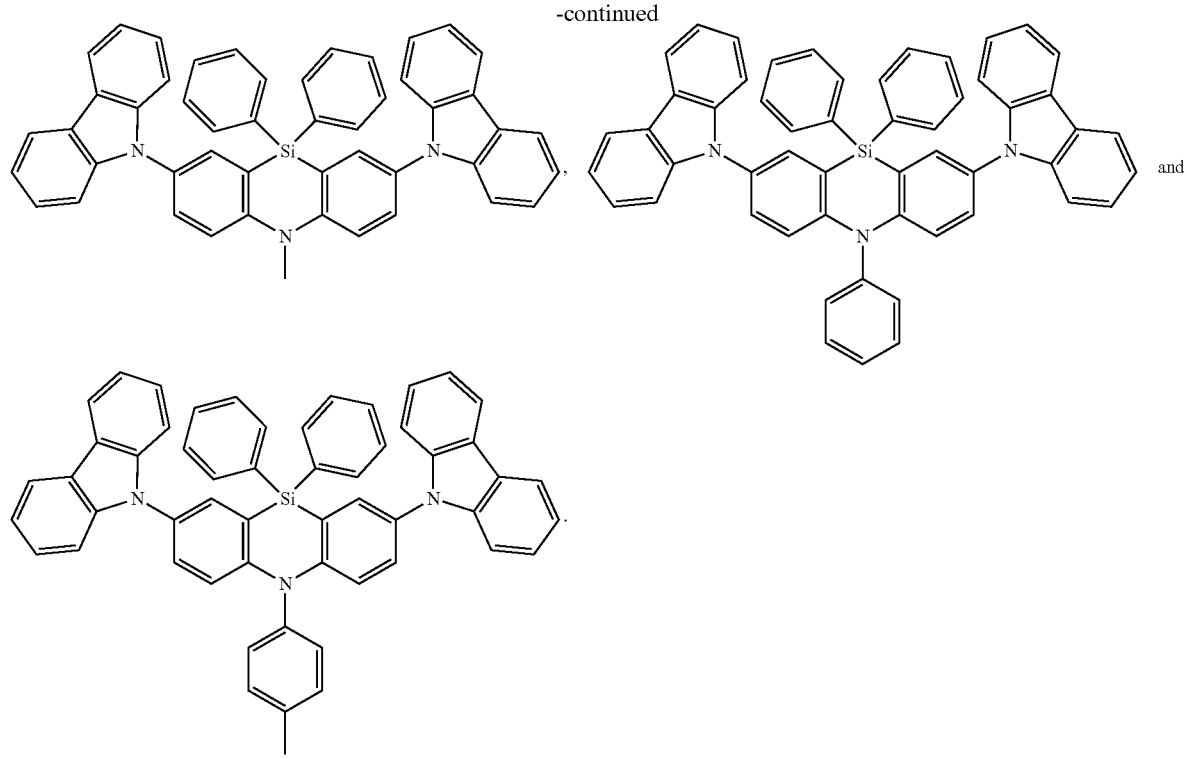
In the above-mentioned compounds T is O, or S, preferably O. If T occurs more than one time in a molecule, all groups T have the same meaning.
The most preferred host compounds are shown below:
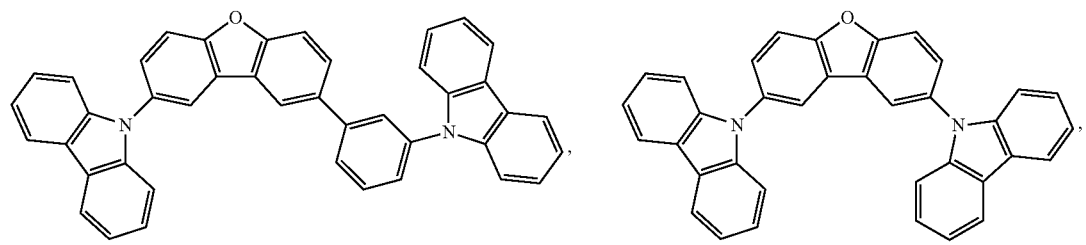
(SH-1)       (SH-2)
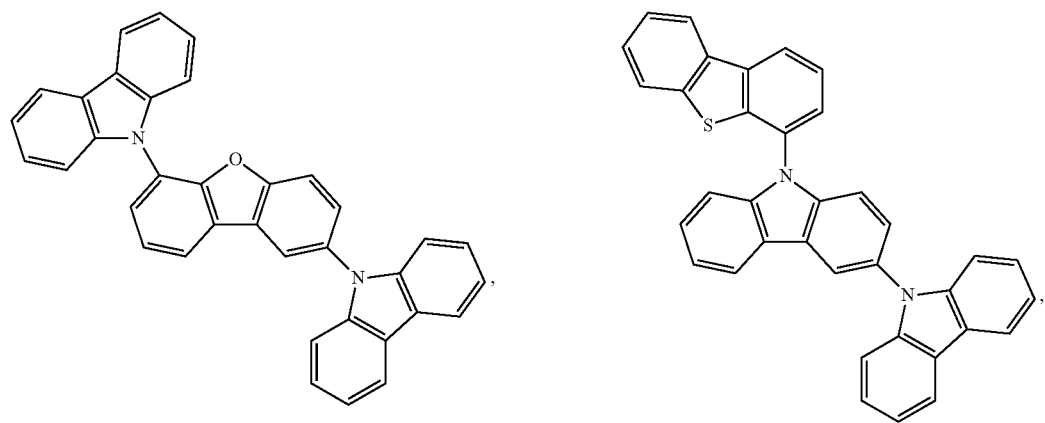
(SH-3), (SH-4), (SH-5), (SH-6)          (SH-7)

(SH-8)
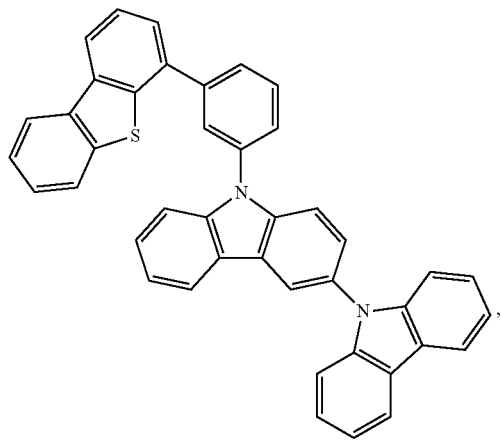
(SH-9)
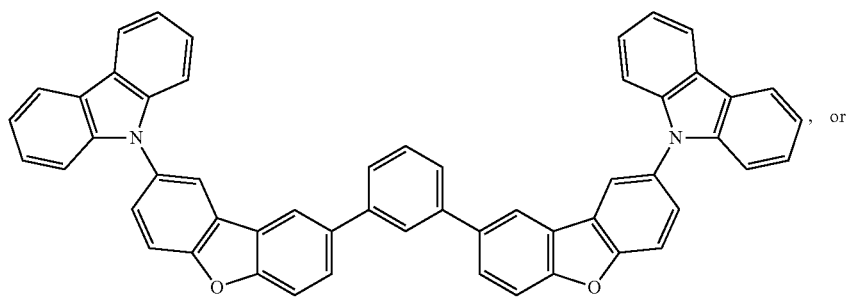, or
(SH-10)
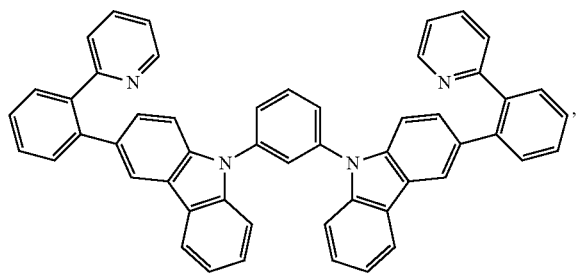
Further host materials, particularly suitable for the fabrication of green to yellow emitting diodes, are
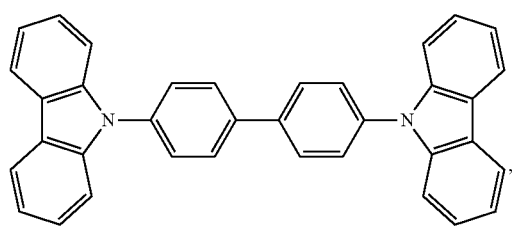
(CBP)
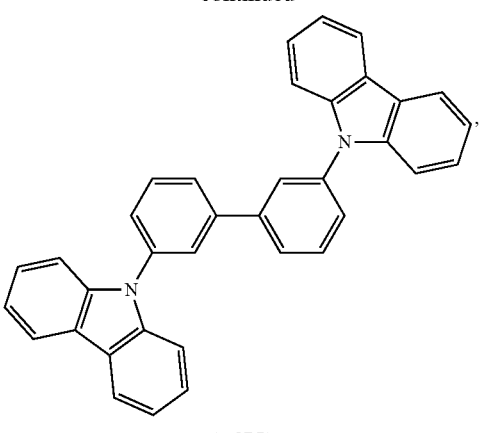
(mCBP)

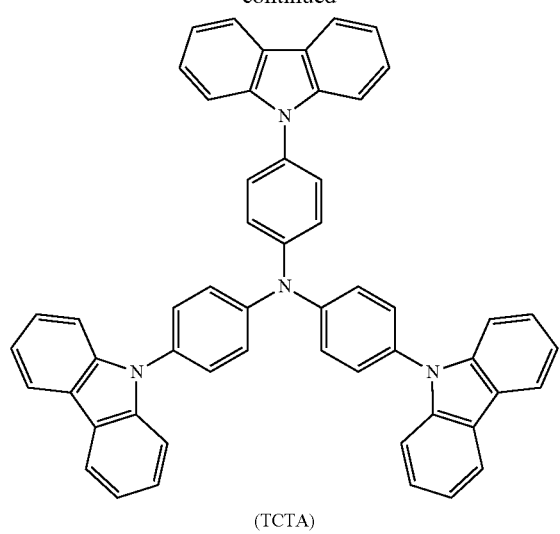
(TCTA)
and Additional host materials are, for example, described in WO2008132965; WO2008140069, WO2012108881, WO2009008099, WO2009008100, US2009017331, U.S. Pat. No. 7,968,213B2, WO2011080972, WO2011122132, WO2011125680, US2011278552, WO2011132683, WO2011132684, WO2011136755, WO2012014841, WO2011137072A1, WO2012023947, WO2012102967 and WO2011093220. Examples of such additional hosts are shown below:
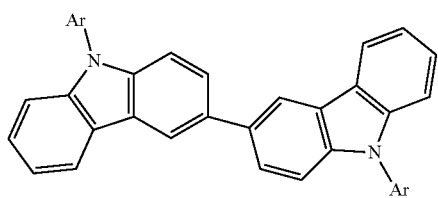
(Ar=aryl, or heteroaryl, such as, for example, pyrimidyl, pyridyl, or triazinyl),
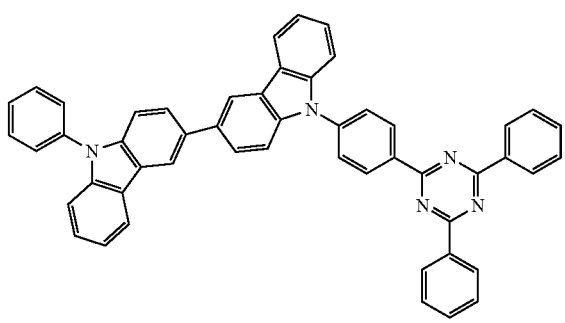
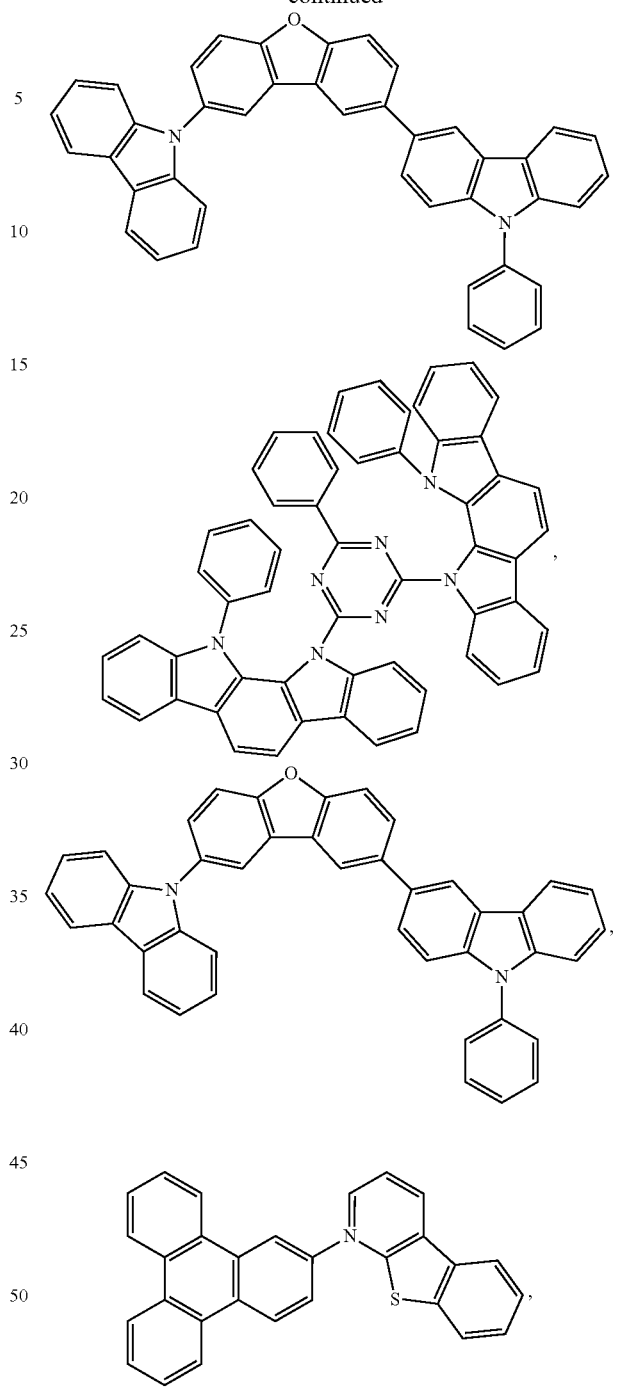
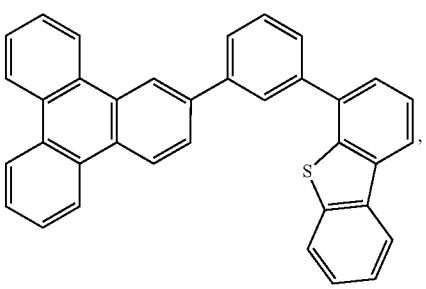

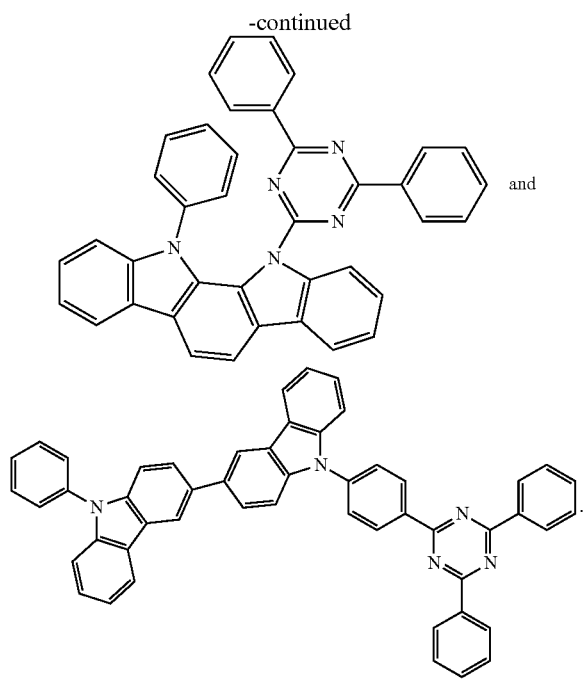

and

In a preferred embodiment, the light-emitting layer is formed from 2 to 40% by weight, preferably 5 to 35% by weight, of at least one of the inventive metal carben complexes and 60 to 98% by weight, preferably 65 to 95% by weight, of at least one of the aforementioned matrix materials, where the sum total of the emitter material and of the matrix material adds up to 100% by weight.

In particularly preferred embodiment, the light-emitting layer comprises a matrix material, such as, for example, compound (SH-1), and two carbene complexes, such as for example, compound EM-1 (or EM-2) and

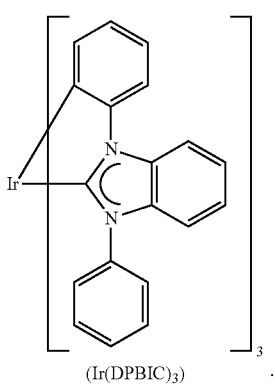

(Ir(DPBIC)$_3$)

In said embodiment, the light-emitting layer is formed from 2 to 40% by weight, preferably 5 to 35% by weight, of EM-1 and 60 to 98% by weight, preferably 65 to 95% by weight, of SH-1 and Ir(DPBIC)$_3$, where the sum total of the carben complexes and SH-1 adds up to 100% by weight.

Suitable metal complexes for use as matrix material and/or hole/exciton blocker material and/or electron/exciton blocker material and/or hole injection material and/or electron injection material and/or hole transport material and/or electron transport material, preferably as matrix material and/or hole/exciton blocker material, in OLEDs are thus, for example, also carbene complexes as described in WO 2005/019373 A2, WO 2006/056418 A2, WO 2005/113704, WO 2007/115970, WO 2007/115981 and WO 2008/000727 and WO2012121936. Explicit reference is made here to the disclosure of the WO applications cited, and these disclosures shall be considered to be incorporated into the content of the present application.

Preferably, the light-emitting layer (e) comprises at least one emitter material and at least one host material. Suitable and preferred emitter materials as well as suitable and preferred host materials are mentioned above.

The individual layers among the aforementioned layers of the OLED may in turn be formed from two or more layers. For example, the hole-transport layer may be formed from one layer, into which holes are injected from the electrode, and a layer which transports the holes away from the hole-injecting layer into the light-emitting layer. The electron-transport layer may likewise consist of a plurality of layers, for example of a layer in which electrons are injected through the electrode and a layer which receives electrons from the electron-injecting layer and transports them into the light-emitting layer. These layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is matched optimally to the inventive metal-carbene complexes used as emitter substances in accordance with the invention.

In order to obtain particularly efficient OLEDs, the HOMO (highest occupied molecular orbital) of the hole-transport layer should be aligned to the work function of the anode, and the LUMO (lowest unoccupied molecular orbital) of the electron-transport layer should be aligned to the work function of the cathode.

The present application further provides an OLED comprising at least one inventive light-emitting layer. The further layers in the OLED may be formed from any material which is typically used in such layers and is known to those skilled in the art.

Suitable materials for the aforementioned layers (anode, cathode, hole and electron injection materials, hole and electron transport materials and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices in Organic Light-Emitting Materials and Devices*, eds: Z. Li, H. Meng, Taylor & Francis, 2007, Chapter 3, pages 295 to 411.

Anode (a)

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

The anode materials mentioned above are commercially available and/or prepared by processes known by a person skilled in the art.

Hole Transport Layer (c)

Suitable hole transport materials for layer (c) of the inventive OLED are disclosed, for example, in Kirk-Othmer Encyclopedia of Chemical Technology, 4th Edition, Vol. 18, pages 837 to 860, 1996. Either hole-transport molecules or polymers may be used as the hole transport material. Customarily used hole-transport molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenyl-hydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino-9,9-spirobifluorene (spiro-TTB), N,N'-bis(naphthalen-1-yl)-N,N'-bis(phenyl)-9,9-spirobifluorene (spiro-NPB) and 9,9-bis(4-(N,N-bis-biphenyl-4-yl-amino)phenyl-9H-fluorene, benzidine compounds such as N,N'-bis(naphthalen-1-yl)-N,N'-bis(phenyl)-benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

In addition—in one embodiment—it is possible to use the inventive metal carbene complexes as hole conductor materials, in which case the band gap of the at least one hole conductor material is generally greater than the band gap of the emitter material used. In the context of the present application, band gap is understood to mean the triplet energy. Suitable carbine complexes are, for example, the inventive carbine complexes of the general formula (I), carbene complexes as described in WO2005/019373A2, WO2006/056418 A2, WO2005/113704, WO2007/115970, WO2007/115981 and WO2008/000727 and WO2012121936. One example of a suitable carbene complex is Ir(DPBIC)₃ with the formula:

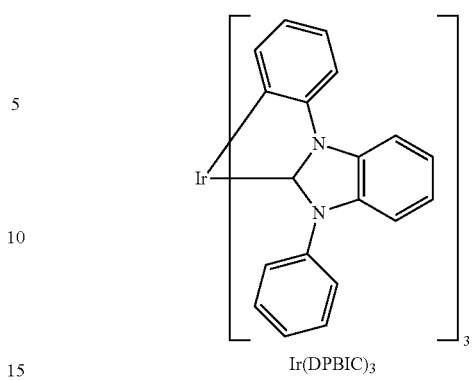

Ir(DPBIC)₃

The hole-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transport layer, in particular mixtures which lead to electrical p-doping of the hole-transport layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WON$, $ReO_3$ and/or $V_2O_5$, preferably $MoO_3$ and/or $ReO_3$, more preferably $ReO_3$ or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane (F4-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquino-dimethane, 2,5-difluoro-7,7,8,8-etracyanoquinodimethane, dicyanomethylene-1,3,4,5,7,8-hexafluoro-6H-naphthalen-2-ylidene)malononitrile ($F_6$-TNAP), Mo(tfd)₃ (from Kahn et al., J. Am. Chem. Soc. 2009, 131 (35), 12530-12531), compounds as described in EP1988587 and in EP2180029 and quinone compounds as mentioned in EP2401254.

Electron-Transport Layer (g)

Electron transport layer may include a material capable of transporting electrons. Electron transport layer may be intrinsic (undoped), or doped. Doping may be used to enhance conductivity. Suitable electron-transport materials for layer (g) of the inventive OLEDs comprise metals chelated with oxinoid compounds, such as tris(8-hydroxyquinolato)aluminum (Alq₃), compounds based on phenanthroline such as 2,9-dimethyl-4,7-diphenyl-1,10phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-

5-(4-t-butylphenyl)-1,3,4-oxadiazole (PBD) and 3-(4-biphenylyl)-4-phenyl-5-(4-t-butylphenyl)-1,2,4-triazole (TAZ). Layer (g) may serve both to ease the electron transport and as a buffer layer or as a barrier layer in order to prevent quenching of the exciton at the interfaces of the layers of the OLED. Layer (g) preferably improves the mobility of the electrons and reduces quenching of the exciton. The electron-transport materials mentioned above are commercially available and/or prepared by processes known by a person skilled in the art.

It is likewise possible to use mixtures of at least two materials in the electron-transport layer, in which case at least one material is electron-conducting. Preferably, in such mixed electron-transport layers, at least one phenanthroline compound is used, preferably BCP (in combination with $Cs_2CO_3$), or at least one pyridine compound according to the formula (VIII) below, preferably a compound of the formula (VIIIaa) below. More preferably, in mixed electron-transport layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII). Reference is made to WO2011/157779.

The electron-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transport layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes and with Y, Ce, Sm, Gd, Tb, Er, Tm, Yb, $Li_3N$, $Rb_2CO_3$, dipotassium phthalate, $W(hpp)_4$ from EP1786050, or with compounds described in EP1837926B1, EP1837927, EP2246862 and WO2010132236.

In a preferred embodiment, the electron-transport layer comprises at least one compound of the general formula (VII)

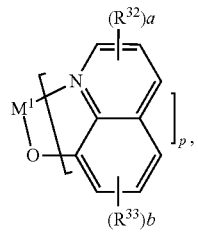

in which
$R^{32}$ and $R^{33}$ are each independently F, $C_1$-$C_8$-alkyl, or $C_6$-$C_{14}$-aryl, which is optionally substituted by one or more $C_1$-$C_8$-alkyl groups, or two $R^{32}$ and/or $R^{33}$ substituents together form a fused benzene ring which is optionally substituted by one or more $C_1$-$C_8$-alkyl groups;
a and b are each independently 0, or 1, 2 or 3,
$M^1$ is an alkaline metal atom or alkaline earth metal atom,
p is 1 when $M^1$ is an alkali metal atom, p is 2 when $M^1$ is an alkali metal atom.

A very particularly preferred compound of the formula (VII) is

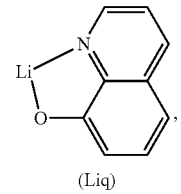

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transport layer comprises at least one compound of the formula (VIII),

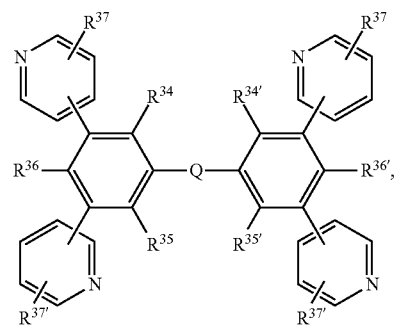

in which
$R^{34}$, $R^{35}$, $R^{36}$, $R^{37}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G, Q is an arylene or heteroarylene group, each of which is optionally substituted by G;
D is —CO—; —COO—; —S—; —SO—; —$SO_2$—; —O—; —$NR^{40}$—; —$SiR^{45}R^{46}$—; —$POR^{47}$—; —$CR^{38}$=$CR^{39}$—; or
E is —$OR^{44}$; —$SR^{44}$; —$NR^{40}R^{41}$; —$COR^{43}$; —$COOR^{42}$; —$CONR^{40}R^{41}$; —CN; or F;
G is E, $C_1$-$C_{18}$-alkyl, $C_1$-$C_{18}$-alkyl which is interrupted by D, $C_1$-$C_{18}$-perfluoroalkyl, $C_1$-$C_{18}$-alkoxy, or $C_1$-$C_{18}$-alkoxy which is substituted by E and/or interrupted by D, in which $R^{38}$ and $R^{39}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;
$R^{40}$ and $R^{41}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or
$R^{40}$ and $R^{41}$ together form a 6-membered ring;

$R^{42}$ and $R^{43}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{44}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{45}$ and $R^{46}$ are each independently $C_1$-$C_{18}$-alkyl, $C_6$-$C_{18}$-aryl or $C_6$-$C_{18}$-aryl which is substituted by $C_1$-$C_{18}$-alkyl, $R^{47}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa)

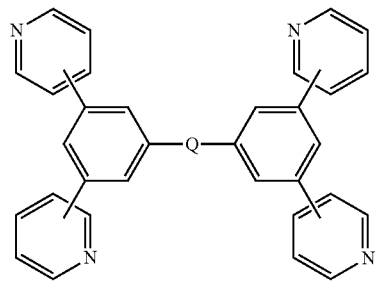
(VIIIa)

in which Q is:

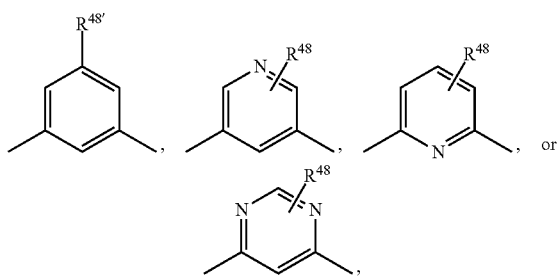

$R^{48}$ is H or $C_1$-$C_{18}$-alkyl and
$R^{48'}$ is H, $C_1$-$C_{18}$-alkyl or

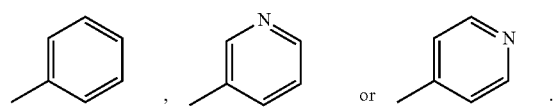

Particular preference is given to a compound of the formula (VIIIaa)

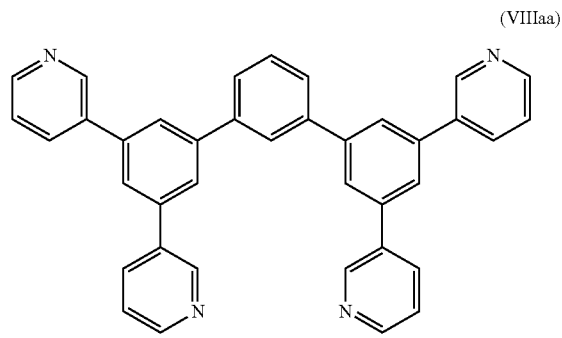 [SMILES: c1cncc(-c2cc(-c3cccnc3)cc(-c3cccc(-c4cc(-c5cccnc5)cc(-c5cccnc5)c4)c3)c2)c1]
(VIIIaa)

In a further, very particularly preferred embodiment, the electron-transport layer comprises a compound of the formula

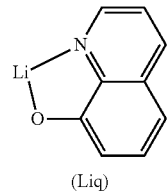
(Liq)

and a compound of the formula

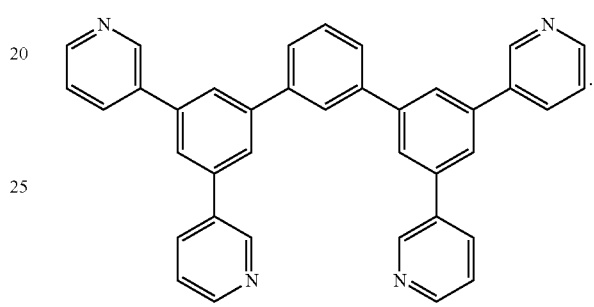
VIIIaa

In a preferred embodiment, the electron-transport layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008-127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transport layer. Reference is made to WO2011/157790. Dibenzofuran compounds A-1 to A-36 and B-1 to B-22 described in WO2011/157790 are preferred, wherein dibenzofuran compound

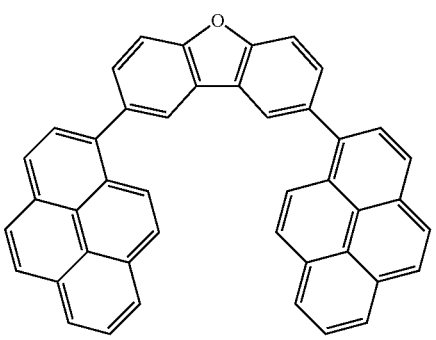
(A-10)

is most preferred.

In a preferred embodiment, the electron-transport layer comprises Liq in an amount of 99 to 1% by weight, preferably 75 to 25% by weight, more preferably about 50% by weight, where the amount of Liq and the amount of the dibenzofuran compound(s), especially compound A-10, adds up to a total of 100% by weight.

In a preferred embodiment, the invention relates to an inventive OLED wherein the electron-transport layer comprises at least one phenanthroline derivative and/or pyridine derivative.

In a further preferred embodiment, the invention relates to an inventive OLED wherein the electron-transport layer comprises at least one phenanthroline derivative and/or pyridine derivative and at least one alkali metal hydroxyquinolate complex.

In a further preferred embodiment, the invention relates to an inventive OLED wherein the electron-transport layer comprises at least one phenanthroline derivative and/or pyridine derivative and 8-hydroxyquinolatolithium.

In a further preferred embodiment, the electron transport layer comprises at least one of the dibenzofuran compounds A-1 to A-36 and B-1 to B-22 described in WO2011/157790, especially A-10.

In a further preferred embodiment, the electron transport layer comprises a compound described in WO 2012/111462, WO 2012/147397 and US 2012/0261654, such as, for example, a compound of formula

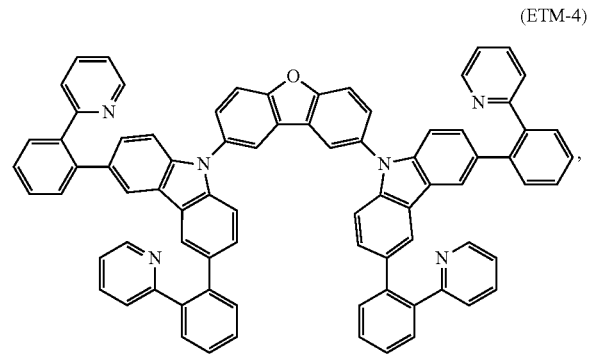 [SMILES: c1ccc(-c2ccccc2-c2ccc3c(c2)c2cc(-c4ccccc4-c4ccccn4)ccc2n3-c2ccc3oc4ccc(-n5c6ccc(-c7ccccc7-c7ccccn7)cc6c6cc(-c7ccccc7-c7ccccn7)ccc65)cc4c3c2)nc1]

(ETM-4)

WO 2012/115034, such as for example, such as, for example, a compound of formula

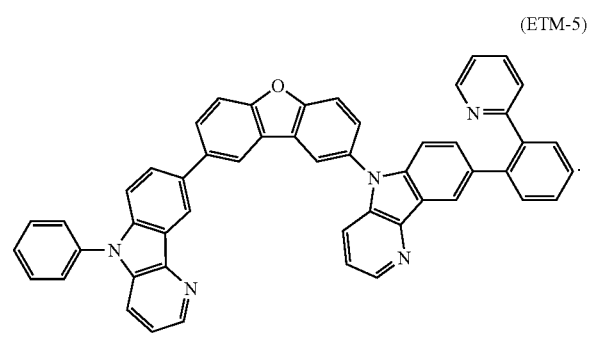 [SMILES: c1ccc(-n2c3ccc(-c4ccc5oc6ccc(-n7c8ccc(-c9ccccc9-c9ccccn9)cc8c8ncccc87)cc6c5c4)cc3c3ncccc32)cc1]

(ETM-5)

Some of the materials mentioned above as hole transport materials and electron-transport materials can fulfill several functions. For example, some of the electron-transport materials are simultaneously hole-blocking materials if they have a low-lying HOMO.

Cathode (i)

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. The cathode materials mentioned above are commercially available and/or prepared by processes known by a person skilled in the art.

Hole Injection Layer (b)

Generally, injection layers are comprised of a material that may improve the injection of charge carriers from one layer, such as an electrode or a charge generating layer, into an adjacent organic layer. Injection layers may also perform a charge transport function. The hole injection layer (b) may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

The hole injection materials mentioned above are commercially available and/or prepared by processes known by a person skilled in the art.

Electron Injection Layer (h)

The electron injection layer (h) may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (i) as an electron injection layer in order to reduce the operating voltage.

The electron injection materials mentioned above are commercially available and/or prepared by processes known by a person skilled in the art.

Those skilled in the art know how suitable materials have to be selected (for example on the basis of electrochemical investigations). Suitable materials for the individual layers are known to those skilled in the art and disclosed, for example, in WO00/70655.

In addition, it is possible that some or all of the layers (b) to (h) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

It is possible that the layers of the OLED are all produced by the same coating method. Furthermore, it is likewise possible to conduct two or more different coating methods to produce the layers of the OLED.

In general, the different layers in the inventive OLED, if present, have the following thicknesses:
anode (a): 50 to 500 nm, preferably 100 to 200 nm;
hole injection layer (b): 5 to 100 nm, preferably 20 to 80 nm;
hole-transport layer (c): 5 to 100 nm, preferably 10 to 80 nm;
electron/exciton blocking layer (d): 1 to 50 nm, preferably 5 to 10 nm,
light-emitting layer (e): 1 to 100 nm, preferably 5 to 60 nm;
hole/exciton blocking layer (f): 1 to 50 nm, preferably 5 to 10 nm,
electron-transport layer (g): 5 to 100 nm, preferably 20 to 80 nm;
electron injection layer (h): 1 to 50 nm, preferably 2 to 10 nm;
cathode (i): 20 to 1000 nm, preferably 30 to 500 nm.

In addition to the compounds of the formula (X), according to the present invention, it is also possible to use crosslinked or polymeric materials comprising repeat units based on the general formula (X) in crosslinked or polymerized form together with at least one inventive metal-carbene complex. Like the compounds of the general formula (X), the latter are preferably used as matrix materials.

The crosslinked or polymeric materials have outstanding solubility in organic solvents, excellent film-forming properties and relatively high glass transition temperatures. In addition, high charge carrier mobilities, high stabilities of color emission and long operating times of the corresponding components can be observed when crosslinked or polymeric materials according to the present invention are used in organic light-emitting diodes (OLEDs).

The crosslinked or polymerized materials are particularly suitable as coatings or in thin films since they are thermally and mechanically stable and relatively defect-free.

The crosslinked or polymerized materials comprising repeating units based on the general formula (X) can be prepared by a process comprising steps (a) and (b):
(a) preparation of a crosslinkable or polymerizable compound of the general formula (X) where at least one of the m1 $R^{204}$ radicals or at least one of the n2 $R^{205}$ radicals is a crosslinkable or polymerizable group attached via a spacer, and (b) crosslinking or polymerization of the compound of the general formula (X) obtained from step (a).

The crosslinked or polymerized materials may be homopolymers, which means that exclusively units of the general formula (X) are present in crosslinked or polymerized form. They may also be copolymers, which means that further monomers are present in addition to the units of the general formula (X), for example monomers with hole-conducting and/or electron-conducting properties, in crosslinked or polymerized form.

In a further preferred embodiment of the inventive OLED, it comprises an emission layer comprising at least one inventive metal-carbene complex, at least one matrix material of the formula (X), and optionally at least one further hole-transport matrix material.

The inventive OLEDs can be used in all devices in which electroluminescence is useful. Suitable devices are preferably selected from stationary and mobile visual display units and illumination means. The present invention therefore also relates to a device selected from the group consisting of stationary visual display units and mobile visual display units and illumination means, comprising an inventive OLED.

Stationary visual display units are, for example, visual display units of computers, televisions, visual display units in printers, kitchen appliances and advertising panels, illuminations and information panels. Mobile visual display units are, for example, visual display units in cellphones, laptops, tablet PCs, digital cameras, mp-3 players, smartphones, vehicles, and destination displays on buses and trains.

The inventive metal-carbene complexes can additionally be used in OLEDs with inverse structure. In these inverse OLEDs, the inventive complexes are in turn preferably used in the light-emitting layer. The structure of inverse OLEDs and the materials typically used therein are known to those skilled in the art.

The present invention further provides a white OLED comprising at least one inventive metal-carbene complex. In a preferred embodiment, the inventive metal-carbene complexes are used as emitter material in the white OLED. Preferred embodiments of the inventive metal-carbene complexes have been specified above. In addition to the at least one inventive metal-carbene complex, the white OLED may comprise (i) at least one compound of the formula (X). The compound of the formula (X) is preferably used as matrix material. Preferred compounds of the formula (X) have been specified above; and/or
(ii) at least one compound of the formula (VII) and/or (IX). The compounds of the formula (VII) and/or (IX) are preferably used as electron transport material. Preferred compounds of the formulae (VII) and (IX) have been specified above.

In order to obtain white light, the OLED must generate light which colors the entire visible range of the spectrum. However, organic emitters normally emit only in a limited portion of the visible spectrum—i.e. are colored. White light can be generated by the combination of different emitters. Typically, red, green and blue emitters are combined. However, the prior art also discloses other methods for formation of white OLEDs, for example the triplet harvesting approach. Suitable structures for white OLEDs or methods for formation of white OLEDs are known to those skilled in the art.

In one embodiment of a white OLED, several dyes are layered one on top of another in the light-emitting layer of an OLED and hence combined (layered device). This can be achieved by mixing all dyes or by direct series connection of different-colored layers. The expression "layered OLED" and suitable embodiments are known to those skilled in the art.

In a further embodiment of a white OLED, several different-colored OLEDs are stacked one on top of another (stacked device). For the stacking of two OLEDs, what is called a charge generation layer (CG layer) is used. This CG layer may be formed, for example, from one electrically n-doped and one electrically p-doped transport layer. The expression "stacked OLED" and suitable embodiments are known to those skilled in the art.

In further embodiments of this "stacked device concept", it is also possible to stack only two OLEDs or to stack more than three OLEDs.

In a further embodiment of white OLEDs, the two concepts mentioned for white light generation can also be combined. For example, a single-color OLED (for example blue) can be stacked with a multicolor layered OLED (for example red-green). Further combinations of the two concepts are conceivable and known to those skilled in the art.

The inventive metal-carbene complexes can be used in any of the layers mentioned above in white OLEDs. In a preferred embodiment, it is used in one or more or all light-emitting layer(s) of the OLED(s), in which case the structure of the invention metal-carbene complex is varied as a function of the use of the complex. Suitable and preferred components for the further layers of the light OLED(s) or materials suitable as matrix material in the light-emitting layer(s) and preferred matrix materials are likewise specified above.

The present invention also relates to an organic electronic device, preferably an organic light-emitting diode (OLED), organic photovoltaic cell (OPV), organic field-effect transistor (OFET) or light-emitting electrochemical cell (LEEC), comprising at least one inventive metal-carbene complex.

EXAMPLES

The examples which follow, more particularly the methods, materials, conditions, process parameters, apparatus and the like detailed in the examples, are intended to support the present invention, but not to restrict the scope of the present invention. All experiments are carried out in protective gas atmosphere. The percentages and ratios mentioned in the examples below—unless stated otherwise—are % by weight and weight ratios.

The synthesis of suitable carbene ligand precursors is well documented in literature. Procedures can be found, for example, in Enders et al., Helvetica Chimica Acta 1996, 79, 61-83, Bielawski et al., Inorg. Chem. 2009, 48, 6924-6933, US2012/319050 and WO2005/019373.

Synthesis of Compounds L-1 to L-6:

Aromatic halide and reagent A are mixed with acetylene B (see Table 1). NaN$_3$ (1.5 eq.) in a round bottom flask (with the exception of Ligand L-3) in a DMSO: H$_2$O (9:1) solution. Next, Na$_2$CO$_3$ (0.2 eq.), sodium ascorbate (0.2 eq), CuSO$_4$×5H$_2$O (0.1 eq.), and L-proline (0.2 eq.) are charged to the reaction mixture. The mixture is stirred at 65° C. for Ligands L-1 to L-5 and at 50° C. for Ligand L-6. The reaction is left to run for 1-3 days. Ice-cold water is added to the mixture after completion to give a yellow precipitate over a brown solution. Gravity filtration is used to separate the product. All products are washed with dilute NH$_4$OH to remove residual azides. The yellow product is left to dry in a vacuum therm overnight at 60° C. (60-90% yield).

TABLE 1

| Compound | Reagent A | Reagent B | Formula | Yield |
|---|---|---|---|---|
| L-1 |  |  |  | 90% |
| L-2 |  |  |  | 60% |
| L-3 |  |  |  | 70% |
| L-4 |  |  |  | 55% |

TABLE 1-continued

| Compound | Reagent A | Reagent B | Formula | Yield |
|---|---|---|---|---|
| L-5 | (phenyl iodide) | (2-ethynylpyridine) | (1-phenyl-4-(2-pyridyl)-1,2,3-triazole) | 63% |
| L-6 | (phenyl iodide) | (4-methyl-2-pentynoic acid) | (1-phenyl-4-isopropyl-1,2,3-triazole) | 10% |

Synthesis of Carbene Precursors CP-1 to CP-7:

The triazole ligand (1 eq.) is placed in a microwave vial along with R-iodide (15 eq.) and acetonitrile at 100-110° C. for 12 hours (see Table 2). Most of the carbene products must be purified before being used in the next step. Ethyl acetate or methyl-tert-butyl ether are usually the most effective solvents, dissolving the impurity and leaving the ligand as a precipitate. The carbene precursor is left to dry overnight in the vacuum therm. The final product following purification is a light yellow color.

TABLE 2

| Carbene Precursor | Compound | R-I | Formula | Yield |
|---|---|---|---|---|
| CP-1 | L-1 | MeI | | 82% |
| CP-2 | L-1 | iPrI | | 43% |
| CP-3 | L-2 | MeI | | 75% |
| CP-4 | L-2 | iPrI | | 33% |
| CP-5 | L-3 | MeI | | 97% |

TABLE 2-continued

| Carbene Precursor | Compound | R-I | Formula | Yield |
|---|---|---|---|---|
| CP-6 | L-4 | MeI | 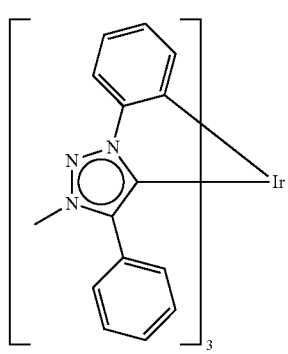 | 67% |
| CP-7 | L-5 | MeI | | 60% |

Example 1

(EM-1)

Anhydrous dichloromethane (100 mL) is added to a round bottom flask and purged with nitrogen. 1.23 g of the triazolium salt L-1 and 0.391 g silver oxide are added and stirred overnight at room temperature. The reaction is monitored via $^1$H-NMR. Once the complexation reaction is completed, 228 mg of [Ir(cod)Cl]$_2$ (1 eq.) and xylene (10 mL) are added to the reaction mixture. After distillation of the dichloromethane, the reaction is heated up to 110° C. under argon atmosphere and monitored by TLC (2:1 cyclohexane:ethyl acetate). Upon completion, the system is cooled to room temperature, the mixture filtered over anhydrous sodium sulfate and the solvent removed via rotary evaporation. The solid is then stirred overnight at room temperature in cyclohexane, filtered, washed with tert-butyl methyl ether and dissolved in dichloromethane. The desired product is obtained as a yellow precipitate (0.42 g) after cooling the solution to 0° C. overnight (yield 70%).

$^1$H-NMR (CD$_2$Cl$_2$): δ=7.67 (d, J=7.7 Hz, 3H), 7.32 (t, J=7.5 Hz, 3H), 7.16 (t, J=6.6 Hz 6H), 7.03-6.89 (m, 6H), 6.84 (t, J=7.2, 3H), 5.98 (d, J=7.7 Hz, 6H), 3.50 (s, 9H) ppm.

$^{13}$C-NMR (CD$_2$Cl$_2$): δ=157.95, 155.41, 146.34, 145.30, 138.90, 130.24, 129.89, 127.88, 127.73, 127.63, 119.65, 113.61, 36.09.

Photoluminexcence (2% in PMMA matrix): λ$_{max}$: 554 nm; CIE$_{x,y}$: 0.44; 0.53; QY: 55%; τ☐ (lifetime of the luminescence): 2.7 ρs.

Example 2

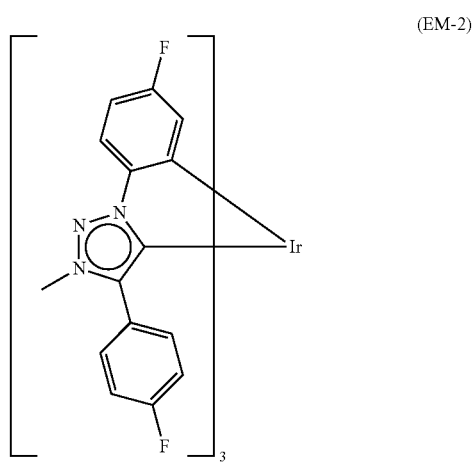

(EM-2)

Anhydrous dichloromethane (120 mL) is added to a round bottom flask and purged with nitrogen. 3.21 g of the triazolium salt L-2 and 2.31 g silver oxide are added and stirred overnight at room temperature. The reaction is monitored via $^1$H-NMR. Once the complexation reaction is completed, 672 mg of [Ir(cod)Cl]$_2$ (1 eq.) and xylene (120 mL) are added to the reaction mixture. After distillation of the dichloromethane, the reaction is heated up to 110° C. under argon atmosphere and monitored by TLC (2:1 cyclohexane: ethyl acetate). Upon completion, the system is cooled to room temperature, the mixture filtered over anhydrous sodium sulfate and silica, using dichloromethane as eluent. After removal of the solvent via rotary evaporation, a solid is obtained, which is stirred overnight at room temperature in ethyl acetate and then filtered, to give 700 mg of the desired product as a yellow precipitate (yield 50%).

$^1$H-NMR (DMSO-d$_6$): δ=7.71-7.55 (m, 3H), 7.13 (t, J=8.8 Hz 6H), 6.81-6.59 (m, 3H), 6.48-6.28 (m, 3H), 6.20-6.02 (m, 6H), 3.63 (s, 9H) ppm.

Photoluminexcence (2% in PMMA matrix): λ$_{max}$: 551 nm; CIE$_{x,y}$: 0.38; 0.53; QY: 81%; τ☐: 4.4 ρs.

Example 3

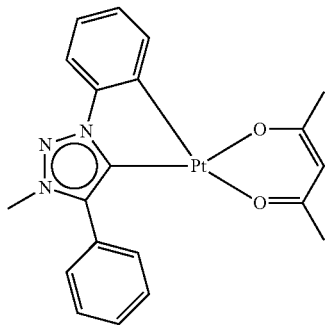
(EM-55)

Anhydrous dichloromethane (35 mL) is added to a round bottom flask and purged with nitrogen. 0.50 g (1.0 eq.) of the triazolium salt L-1 and 0.40 g (1.25 eq.) silver oxide are added and stirred overnight at room temperature. The reaction is monitored via $^1$H-NMR. Once the complexation reaction is completed, the solvent is evaporated and 2-butanone (17.5 mL) and 0.52 g (1 eq.) of Pt(cod)Cl$_2$ are added and the reaction refluxed overnight. After cooling to room temperature, the solvent is evaporated and 34.5 mL anhydrous DMF added together with 0.55 g (4 eq.) 2,4-pentandione and 0.62 g (4 eq.) potassium tert-butylate. The reaction is stirred at room temperature for 21 hours and then heated up to 100° C. for 6 hours. After cooling to room temperature the reaction is filtered, the solvent removed and the so obtained solid washed first with water an then with petroleum ether. The desired product is obtained after column chromatographic purification over silica using dichloromethane and ethyl acetate (0.15 g, yield 20%).

$^1$H-NMR (acetone-d$_6$): δ=7.82-7.72 (m, 3H), 7.59-7.52 (m, 3H), 7.46-7.36 (m, 1H), 7.13-7.03 (m, 2H), 5.47-5.30 (s, 1H), 4.30-4.13 (s, 3H), 1.97-1.85 (s, 3H), 1.58-1.47 (s, 3H) ppm.

Photoluminexcence (2% in PMMA matrix): $\lambda_{max}$: 495 nm; CIE$_{x,y}$: 0.23; 0.44; QY: 78%; τ☐: 8.7 ρs.

Application Examples

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer AJ20-1000 from Plexcore is spun on from solution.

Thereafter, the organic materials specified below are applied by vapor deposition to the cleaned substrate at about $10^{-7}$-$10^{-9}$ mbar at a rate of approx. 0.5-5 nm/min.

The hole conductor and exciton blocker applied to the substrate is

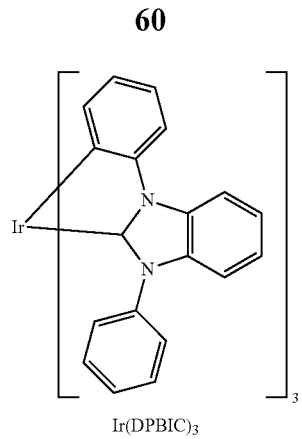
Ir(DPBIC)$_3$ (for preparation of Ir(DPBIC)$_3$ see Ir complex (7) in the application WO2005/19373) with a thickness of 20 nm, of which the first 10 nm are doped with MoO$_3$ to improve the conductivity. Subsequently, a mixture of emitter Em1 (10% by wt.), Ir(DPBIC)$_3$ (10% by wt.), and compound

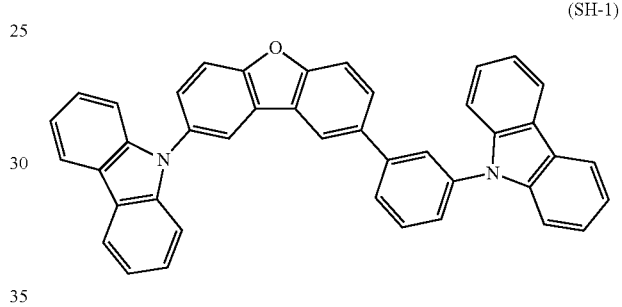
(SH-1)

(80% by wt) is applied by vapor deposition with a thickness of 40 nm, the latter compounds functioning as matrix materials. Subsequently, the material SH-1 is applied by vapor deposition with a thickness of 5 nm as a hole blocker. Next, as an electron transporting layer, a mixture of Cs$_2$CO$_3$ (7% by wt.) and

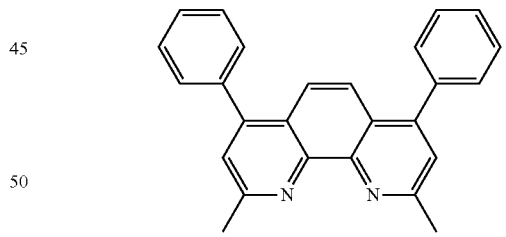

(BCP; 93% by wt.) is applied by vapor deposition and finally a 100 nm-thick Al electrode. All components are adhesive-bonded to a glass lid in an inert nitrogen atmosphere.

The obtained device (Device 1) has the following architecture:
ITO-Plexcore AJ20-1000—10 nm Ir(DPBIC)$_3$:MoO$_3$ (90:10)—10 nm Ir(DPBIC)$_3$—40 nm EM-1/SH-1/Ir(DPBIC)$_3$ (10:80:10)—5 nm SH-1—20 nm BCP:Cs$_2$CO$_3$ (93:7)—100 nm Al

Application Examples 2 to 5

Devices 2 to 5 are obtained in analogy to Application Example 1. The device architecture of Devices 2 to 5 is shown below:

Device 2:

ITO-Plexcore AJ20-1000—10 nm Ir(DPBIC)$_3$:MoO$_3$ (90:10)—10 nm Ir(DPBIC)$_3$—40 nm EM-1/mCBP (10:90)—5 nm mCBP—20 nm BCP:Cs$_2$CO$_3$ (93:7)—100 nm Al Device 3:

ITO-Plexcore AJ20-1000—10 nm Ir(DPBIC)$_3$:MoO$_3$ (90:10)—10 nm Ir(DPBIC)$_3$—40 nm EM-2/SH-1/Ir(DPBIC)$_3$ (10:75:15)—5 nm SH-1—30 nm BCP:Cs$_2$CO$_3$ (95:5)—100 nm Al Device 4:

ITO-Plexcore AJ20-1000—10 nm Ir(DPBIC)$_3$:MoO$_3$ (90:10)—10 nm Ir(DPBIC)$_3$—40 nm

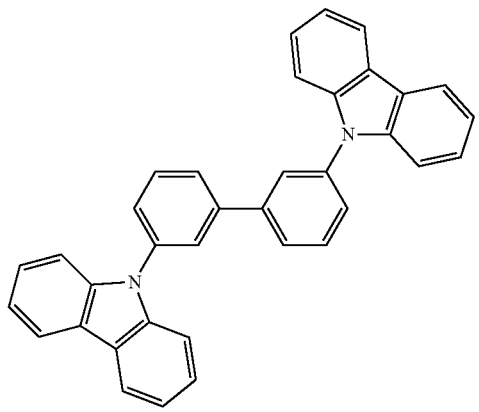 [SMILES: c1cc(-c2cccc(-n3c4ccccc4c4ccccc43)c2)cc(-n2c3ccccc3c3ccccc32)c1]

EM-2/(mCBP)/SH-1 (10:30:60)—5 nm SH-1—20 nm (A-10)

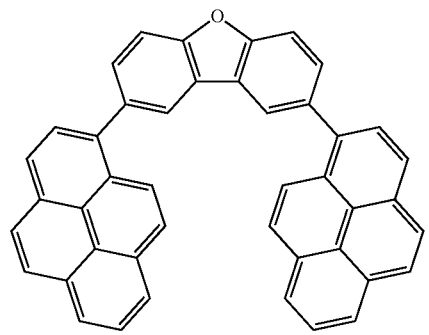

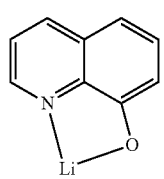

(Liq; 50:50)—2 nm KF—100 nm Al

Device 5:

ITO-Plexcore AJ20-1000—10 nm Ir(DPBIC)$_3$:MoO$_3$ (90:10)—10 nm TCTA—40 nm

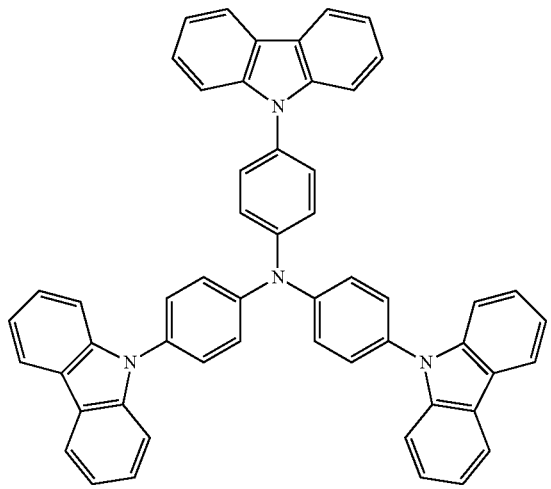 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1]

EM-2/(TCTA; 10:90)—5 nm SH-1—25 nm A-10:Liq (50:50)—2 nm KF—100 nm Al

To characterize the OLED, electroluminescence spectra are recorded at different currents and voltages. In addition, the current-voltage characteristic is measured in combination with the light output emitted. The light output can be converted to photometric parameters by calibration with a photometer.

Voltage (V), current efficiency (cd/A), External Quantum Efficiency (EQE) (%), $\lambda_{max}$ (nm) and CIE$_{x,y}$ measured for the devices of the Application Examples and Comparative Application Examples at 1000 nits are shown in the Table 3 below.

TABLE 3

| Example | Voltage [V] | CurrEff [cd/A] | EQE[1] [%] | $\lambda_{max}$ [nm] | CIE$_{x,y}$ |
|---|---|---|---|---|---|
| Device 1 | 3.9 | 29.9 | 10.8 | 589 | 0.45; 0.53 |
| Device 2 | 4.8 | 27.0 | 9.7 | 588 | 0.45; 0.53 |
| Device 3 | 3.4 | 29.1 | 10.4 | 578 | 0.42; 0.52 |
| Device 4 | 3.3 | 33.4 | 11.6 | 572 | 0.40; 0.53 |
| Device 5 | 4.4 | 30.5 | 11.0 | 578 | 0.42; 0.52 |

[1] External quantum efficiency (EQE) is # a of generated photons escaped from a substance or a device/# of electrons flowing through it.

Similar results can be achieved with inventive platinum metal carben complexes.

The invention claimed is:

1. A metal-carbene complex of the general formula (I)

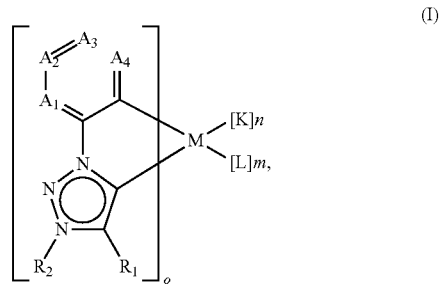

wherein

M is Ir or Pt, $R_1$ and $R_2$ are independently of each other a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical, optionally bearing at least one functional group and having 6 to 30 carbon atoms, substituted or unsubstituted heteroaryl radical optionally interrupted by at least one heteroatom, optionally bearing at least one functional group and having a total of 5 to 18 ring atoms, $A_1$, $A_2$, $A_3$ and $A_4$ are independently from each other $CR_3$ or N;

each $R_3$ is independently of each other H, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 ring atoms; or a group with donor or acceptor action;

K and L are independently from each other a bidentate monoanionic ligand;

for M is Ir, o is 1, 2 or 3, m is 0, 1, or 2, n is 0, 1, or 2 and m+n+o=3 and for M is Pt, o is 1, or 2, m is 0, or 1, n is 0, or 1 and m+n+o=2.

2. The metal-carbene complex according to claim 1, which is a metal-carbene complex of the general formula

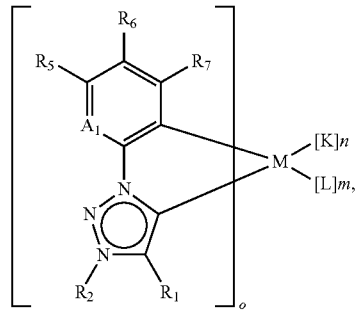

(II)

wherein $A_1$ is N, or $CR_4$, $R_4$, $R_5$, $R_6$ and $R_7$ are independently of each other H, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 ring atoms; or a group with donor or acceptor action and $R_1$, $R_2$, M, L, n, m and o are as defined in claim 1.

3. The metal complex according to claim 2, which is a metal-carbene complex of the general formula

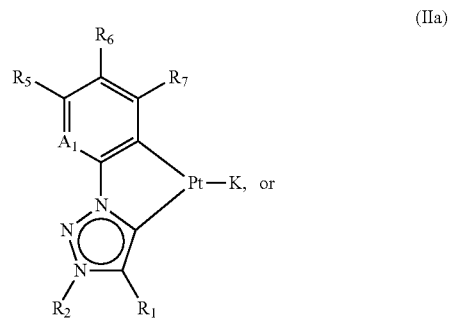

(IIa)

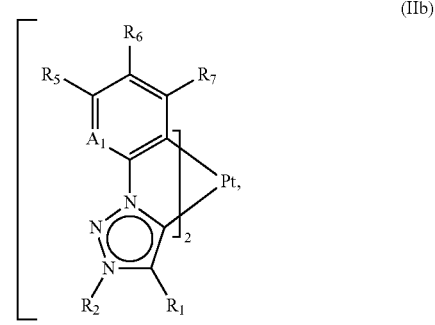

(IIb)

wherein

K is a bidentate monoanionic ligand of formula

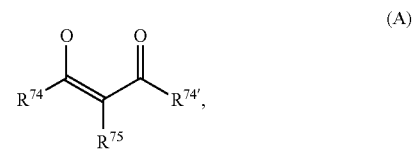

(A)

in which $R^{74}$ and $R^{74'}$ are in each case independently a linear or branched alkyl radical having 1 to 6 carbons atoms optionally bearing at least one functional group; substituted or unsubstituted cycloalkyl radical having 3 to 20 carbon atoms, substituted or unsubstituted aryl radical having 6 to 20 carbon atoms; substituted or unsubstituted heteroaryl radical having a total of 5 to 18 ring atoms, and $R^{75}$ is hydrogen, a linear or branched alkyl radical having 1 to 6 carbon atoms, substituted or unsubstituted aryl radical having 6 to 20 carbon atoms;

$A_1$ is N, or $CR_4$, $R_4$, $R_5$, $R_6$ and $R_7$ are independently of each other H, a linear or branched alkyl radical optionally interrupted by at least one heteroatom, optionally bearing at least one functional group and having 1 to 6 carbon atoms, substituted or unsubstituted cycloalkyl radical optionally interrupted by at least one heteroatom, optionally bearing at least one functional group and having 3 to 12 carbon atoms, substituted or unsubstituted aryl radical optionally interrupted by at least one heteroatom, optionally bearing at least one functional group and having 6 to 15 carbon atoms, substituted or unsubstituted heteroaryl radical optionally interrupted by at least one heteroatom, optionally bearing at least one functional group and having a total of 5 to 15 ring atoms; or a group with donor or acceptor action, selected from halogen radicals, $SiMe_3$, $SiPh_3$, OMe, $NO_2$, CN, NCO, NCS, $CF_3$, and $R_1$ and $R_2$ are independently of each other a linear or branched alkyl radical optionally interrupted by at least one heteroatom, optionally bearing at least one functional group and having 1 to 6 carbon atoms, substituted or unsubstituted cycloalkyl radical optionally interrupted by at least one heteroatom, optionally beating at least one functional group and having 3 to 12 carbon atoms, substituted or unsubstituted aryl radical, optionally bearing at least one functional group and having 6 to 15 carbon atoms, substituted or unsubstituted heteroaryl radical optionally interrupted by at least one heteroatom, optionally bearing at least one functional group and having a total of 5 to 15 carbon atoms.

4. The metal complex according to claim 2, which is a metal-carbene complex of the general formula

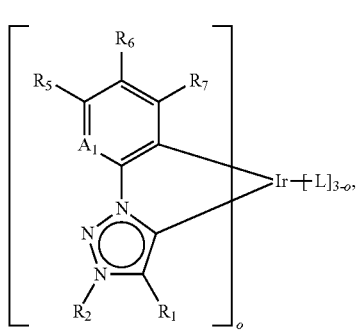

(IIc)

wherein o is 1, 2, or 3,

L is a bidentate monoanionic ligand of formula

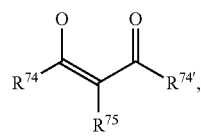

in which $R^{74}$ and $R^{74'}$ are in each case independently a linear or branched alkyl radical having 1 to 6 carbons atoms optionally bearing at least one functional group; substituted or unsubstituted cycloalkyl radical having 3 to 20 carbon atoms, substituted or unsubstituted aryl radical having 6 to 20 carbon atoms; substituted or unsubstituted heteroaryl radical having a total of 5 to 18 ring atoms, and $R^{75}$ is hydrogen, a linear or branched alkyl radical having 1 to 6 carbon atoms, substituted or unsubstituted aryl radical having 6 to 20 carbon atoms; or L is a bidentate monoanionic ligand of formula

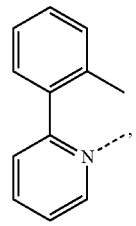

(X-1)

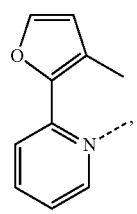

(X-2)

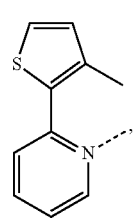

(X-3)

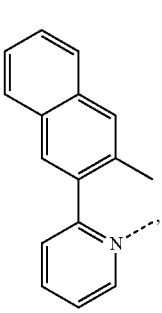

(X-4)

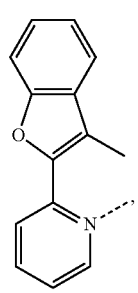

(X-5)

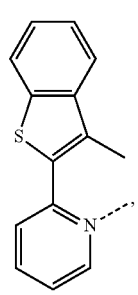

(X-6)

(X-7) 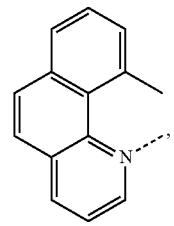
(X-8) 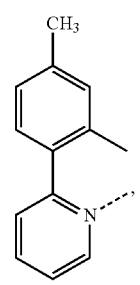
(X-9) 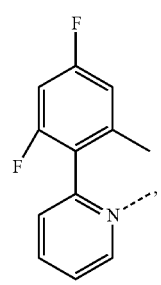
(X-10) 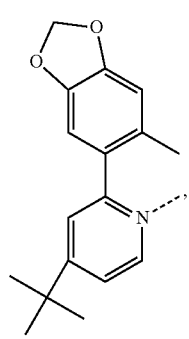
(X-11) 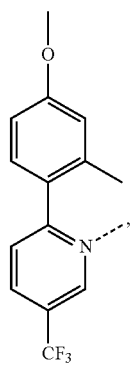
(X-12) 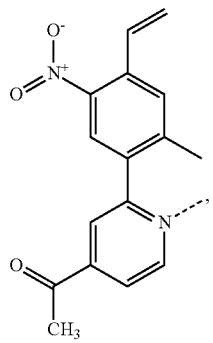
(X-13) 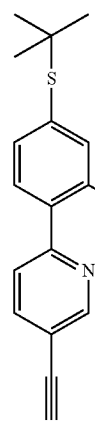
(X-14) 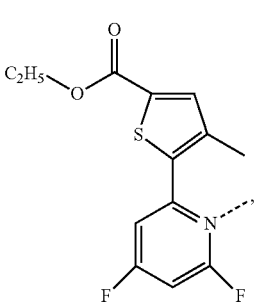
(X-15) 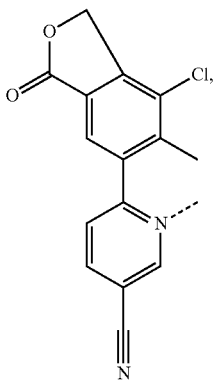

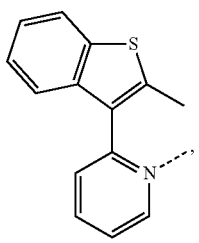 (X-16)
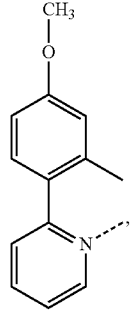 (X-17)
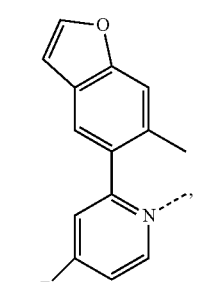 (X-18)
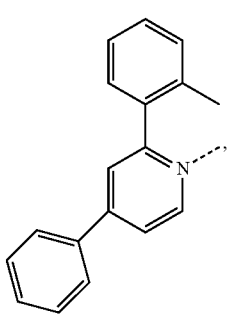 (X-19)
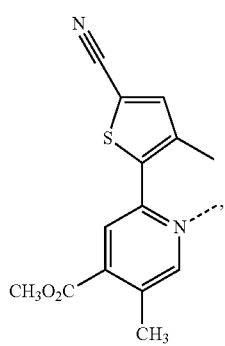 (X-20)
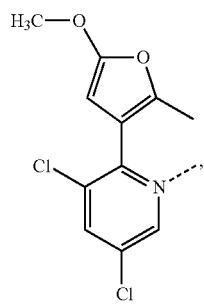 (X-21)
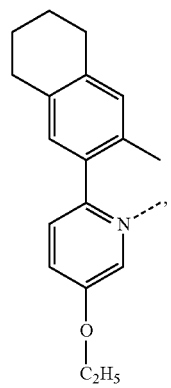 (X-22)
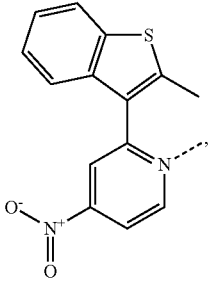 (X-23)
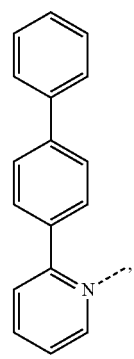 (X-24)

(X-25) 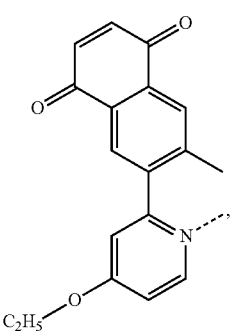
(X-26) 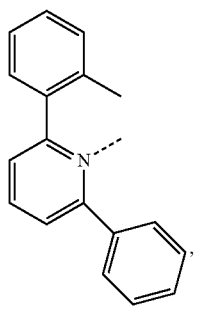
(X-27) 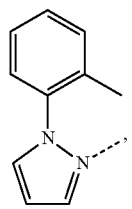
(X-28) 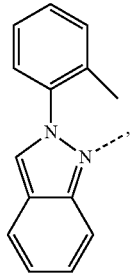
(X-29) 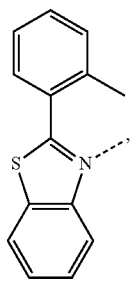
(X-30) 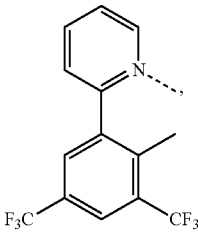
(X-31) 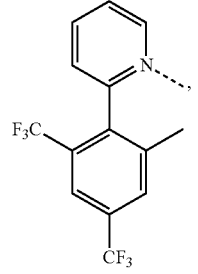
(X-32)
(X-33)
(X-34)
(X-35)

(X-36)
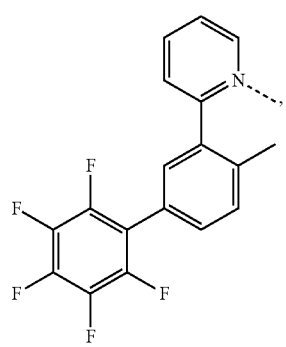
(X-37)
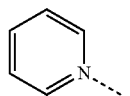
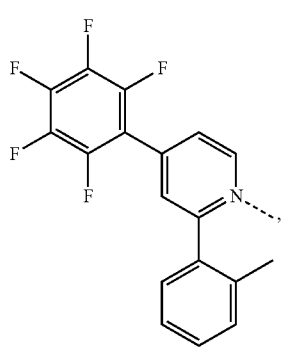
(X-37')
(X-38)
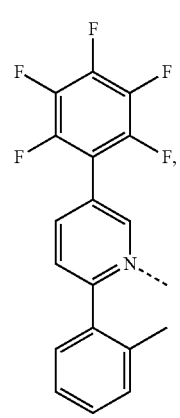
(X-39)
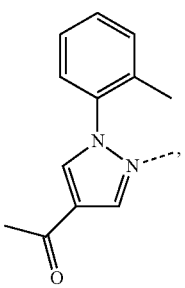
(X-40)
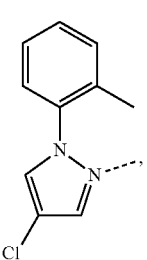
(X-41)
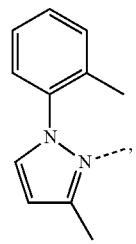
(X-42)
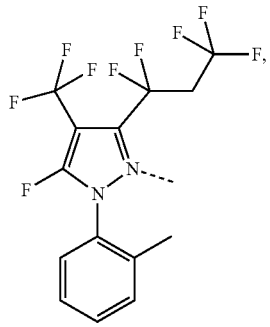
(X-43)
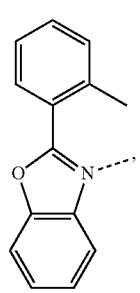

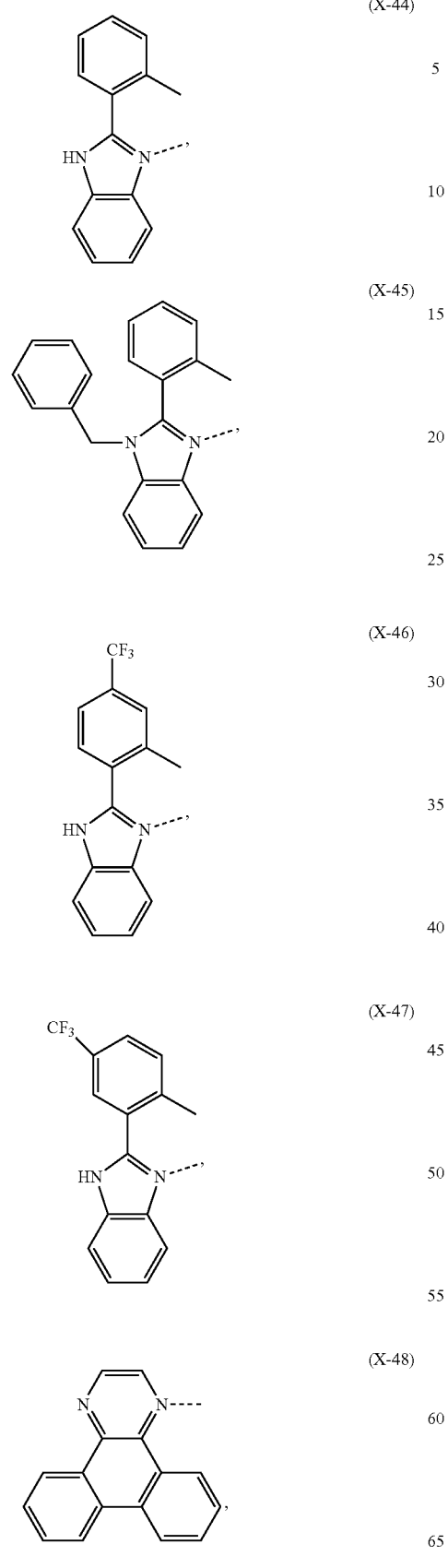
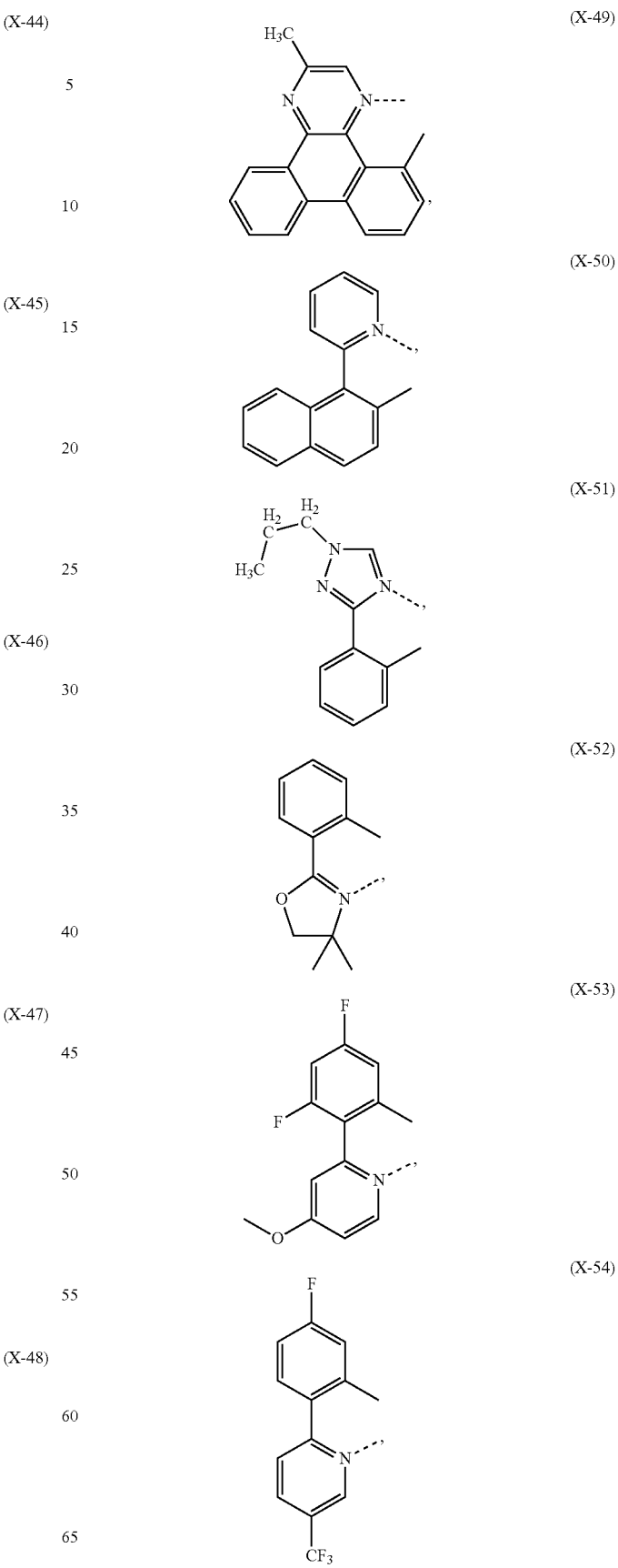

(X-55) 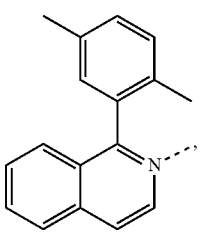

(X-56) 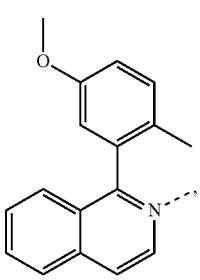

(X-57) 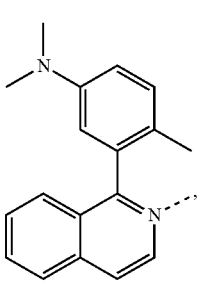

(X-58) 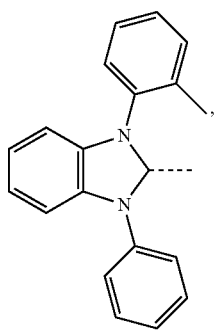

(X-58) 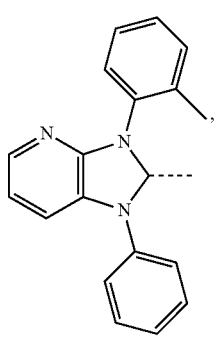

(X-59) 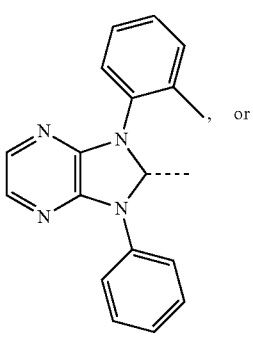

(X-60) 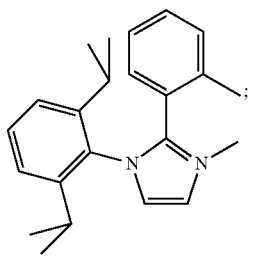

$A_1$ is N, or $CR_4$, $R_4$, $R_5$, $R_6$ and $R_7$ are independently of each other H, a linear or branched alkyl radical optionally interrupted by at least one heteroatom, optionally bearing at least one functional group and having 1 to 6 carbon atoms, substituted or unsubstituted cycloalkyl radical optionally interrupted by at least one heteroatom, optionally bearing at least one functional group and having 3 to 12 carbon atoms, substituted or unsubstituted aryl radical optionally interrupted by at least one heteroatom, optionally bearing at least one functional group and having 6 to 15 carbon atoms, substituted or unsubstituted heteroaryl radical optionally interrupted by at least one heteroatom, optionally bearing at least one functional group and having a total of 5 to 15 ring atoms; or a group with donor or acceptor action, selected from halogen radicals, $SiMe_3$, $SiPh_3$, OMe, $NO_2$, CN, NCO, NCS, $CF_3$, and $R_1$ and $R_2$ are independently of each other a linear or branched alkyl radical optionally interrupted by at least one heteroatom, optionally beating at least one functional group and having 1 to 6 carbon atoms, substituted or unsubstituted cycloalkyl radical optionally interrupted by at least one heteroatom, optionally bearing at least one functional group and having 3 to 12 carbon atoms, substituted or unsubstituted aryl radical, optionally bearing at least one functional group and having 6 to 15 carbon atoms, substituted or unsubstituted heteroaryl radical optionally interrupted by at least one heteroatom, optionally bearing at least one functional group and having a total of 5 to 15 ring atoms.

5. The metal complex according to claim 4, which is a metal-carbene complex of the general formula

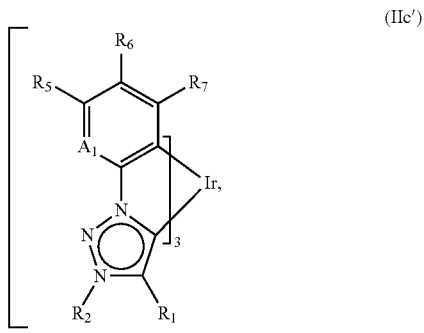

(IIc′)

wherein

R₁, R₂, R₅, R₆, R₇, and A₁ are as defined in claim 4.

6. The metal complex according to claim 2, wherein $R_7$ is hydrogen.

7. The metal complex according to claim 2, wherein $A_1$ is $CR_4$, wherein $R_4$ is hydrogen, a linear or branched alkyl radical having 1 to 6 carbon atoms, substituted or unsubstituted aryl radical having 6 to 15 carbon atoms, or a group with donor or acceptor action selected from CN, $CF_3$, $SiMe_3$, halogen radicals.

8. The metal complex according to claim 2, wherein $R_5$ is hydrogen, a linear or branched alkyl radical having 1 to 6 carbon atoms, substituted or unsubstituted aryl radical having 6 to 15 carbon atoms, or a group with donor or acceptor action selected from CN, $CF_3$, $SiMe_3$, halogen radicals.

9. The metal complex according to claim 2, wherein $R_6$ is hydrogen, a linear or branched alkyl radical having 1 to 6 carbon atoms, substituted or unsubstituted aryl radical having 6 to 15 carbon atoms, or a group with donor or acceptor action selected from CN, $CF_3$, $SiMe_3$, halogen radicals.

10. The metal-carbene complex according to claim 1, wherein
    $R_1$ is a linear or branched alkyl radical having 1 to 6 carbon atoms, a substituted or unsubstituted aryl radical having 6 to 20 carbon atoms, a substituted or unsubstituted heteroaryl radical having a total of 5 to 18 ring atoms.

11. The metal-carbene complex according to claim 1, wherein
    $R_2$ is a linear or branched alkyl radical having 1 to 6 carbons atoms, or a unsubstituted aryl radical having 6 to 15 carbon atoms.

12. The metal-carbene complex according to claim 1, which is a compound of formula

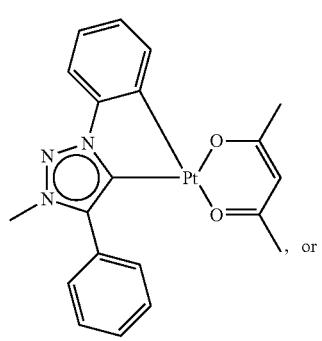

(EM-55)

, or

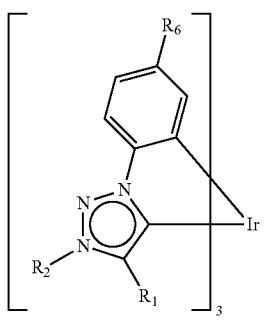

| Compound | R₁ | R₂ | R₆ |
|---|---|---|---|
| EM-1 | phenyl | CH₃ | H |
| EM-2 | 4-F-phenyl | CH₃ | H |
| EM-3 | 2-F-phenyl | CH(CH₃)₂ | H |
| EM-4 | 4-CF₃-phenyl | CH(CH₃)₂ | H |
| EM-5 | 2-CF₃-phenyl | CH(CH₃)₂ | H |
| EM-6 | 2-CH₃-phenyl | CH(CH₃)₂ | H |
| EM-7 | pyridyl | CH(CH₃)₂ | H |
| EM-8 | 4-F-phenyl | CH(CH₃)₂ | H |
| EM-9 | 2-F-phenyl | CH₃ | H |

| Compound | R₁ | R₂ | R₆ |
|---|---|---|---|
| EM-10 | 4-(CF₃)C₆H₄- | CH₃ | H |
| EM-11 | 2-(CF₃)C₆H₄- | CH₃ | H |
| EM-12 | 2-(CH₃)C₆H₄- | CH₃ | H |
| EM-13 | C₆H₅- | C₆H₅- | H |
| EM-14 | 4-F-C₆H₄- | C₆H₅- | H |
| EM-15 | 2-F-C₆H₄- | C₆H₅- | H |
| EM-16 | 4-(CF₃)C₆H₄- | C₆H₅- | H |
| EM-17 | 2-(CF₃)C₆H₄- | C₆H₅- | H |
| EM-18 | 2-(CH₃)C₆H₄- | C₆H₅- | H |
| EM-19 | C₆H₅- | CH(CH₃)₂ | F |
| EM-20 | 4-F-C₆H₄- | CH(CH₃)₂ | F |
| EM-21 | 2-F-C₆H₄- | CH(CH₃)₂ | F |

| Compound | R₁ | R₂ | R₆ |
|---|---|---|---|
| EM-22 | 4-(CF₃)C₆H₄- | CH(CH₃)₂ | F |
| EM-23 | 2-(CF₃)C₆H₄- | CH(CH₃)₂ | F |
| EM-24 | 2-(CH₃)C₆H₄- | CH(CH₃)₂ | F |
| EM-25 | C₆H₅- | CH₃ | F |
| EM-26 | 4-F-C₆H₄- | CH₃ | F |
| EM-27 | 2-F-C₆H₄- | CH₃ | F |
| EM-28 | 4-(CF₃)C₆H₄- | CH₃ | F |
| EM-29 | 2-(CF₃)C₆H₄- | CH₃ | F |
| EM-30 | 2-(CH₃)C₆H₄- | CH₃ | F |
| EM-31 | C₆H₅- | C₆H₅- | F |
| EM-32 | 4-F-C₆H₄- | C₆H₅- | F |
| EM-33 | 2-F-C₆H₄- | C₆H₅- | F |

-continued

| Compound | R₁ | R₂ | R₆ |
|---|---|---|---|
| EM-34 | 4-(CF₃)-phenyl | phenyl | F |
| EM-35 | 2-(CF₃)-phenyl | phenyl | F |
| EM-36 | 2-(CH₃)-phenyl | phenyl | F |
| EM-37 | phenyl | CH(CH₃)₂ | CF₃ |
| EM-38 | 4-F-phenyl | CH(CH₃)₂ | CF₃ |
| EM-39 | 2-F-phenyl | CH(CH₃)₂ | CF₃ |
| EM-40 | 4-(CF₃)-phenyl | CH(CH₃)₂ | CF₃ |
| EM-41 | 2-(CF₃)-phenyl | CH(CH₃)₂ | CF₃ |
| EM-42 | 2-(CH₃)-phenyl | CH(CH₃)₂ | CF₃ |
| EM-43 | phenyl | CH₃ | CF₃ |
| EM-44 | 4-F-phenyl | CH₃ | CF₃ |
| EM-45 | 2-F-phenyl | CH₃ | CF₃ |
| EM-46 | 4-(CF₃)-phenyl | CH₃ | CF₃ |
| EM-47 | 2-(CF₃)-phenyl | CH₃ | CF₃ |
| EM-48 | 2-(CH₃)-phenyl | CH₃ | CF₃ |
| EM-49 | phenyl | phenyl | CF₃ |
| EM-50 | 4-F-phenyl | phenyl | CF₃ |
| EM-51 | 2-F-phenyl | phenyl | CF₃ |
| EM-52 | 4-(CF₃)-phenyl | phenyl | CF₃ |
| EM-53 | 2-(CF₃)-phenyl | phenyl | CF₃ |
| EM-54 | 2-(CH₃)-phenyl | phenyl | CF₃. |

13. An organic electronic device, comprising at least one metal-carbene complex according to claim 1.

14. The organic electronic device according to claim 13, wherein the organic electronic device is selected from organic light-emitting diodes (OLEDs), organic photovoltaic cells (OPVs), organic field-effect transistors (OFETs) and light-emitting electrochemical cells (LEECs).

15. A light-emitting layer comprising at least one metal-carbene complex according to claim 1.

16. The light-emitting layer according to claim 15, further comprising a host material.

17. An apparatus selected from the group consisting of stationary visual display units, illuminations, information panels, and mobile visual display units, illumination units; keyboards; items of clothing; furniture and wallpaper, comprising the organic electronic device according to claim 13.

18. A method of using the metal-carbene complex according to claim 1, comprising:
adding the metal-carbene complex to electrophotographic photoreceptors, photoelectric converters, organic solar cells (organic photovoltaics), switching elements, organic light emitting field effect transistors (OLEFETs), image sensors, dye lasers and electroluminescent devices.

19. A process for preparing a metal-carbene complex according to claim 1 by contacting a suitable compound comprising M with a compound of the general formula

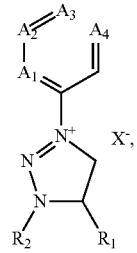

(IV)

wherein
$A_1, A_2, A_3, A_4, R_1, R_2$ and M are as defined in claim 1, and
X is F, CA, Br, I, $PF_6$, or $BF_4$.

20. An apparatus selected from the group consisting of stationary visual display units, illuminations, information panels, and mobile visual display units, illumination units; keyboards; items of clothing; furniture and wallpaper, comprising the light-emitting layer according to claim 15.

* * * * *